(12) United States Patent
Breitenbucher et al.

(10) Patent No.: US 7,250,434 B2
(45) Date of Patent: Jul. 31, 2007

(54) CCK-1 RECEPTOR MODULATORS

(75) Inventors: J. Guy Breitenbucher, Escondido, CA (US); Michael D. Hack, San Diego, CA (US); Clark A. Sehon, West Chester, PA (US)

(73) Assignee: Janssen Pharmaceutica N.V. (BE)

( * ) Notice: Subject to any disclaimer, the term of this patent is extended or adjusted under 35 U.S.C. 154(b) by 405 days.

(21) Appl. No.: 11/018,049

(22) Filed: Dec. 21, 2004

(65) Prior Publication Data

US 2005/0197377 A1 Sep. 8, 2005

Related U.S. Application Data

(60) Provisional application No. 60/531,795, filed on Dec. 22, 2003.

(51) Int. Cl.
*A61K 31/4172* (2006.01)
*C07D 233/64* (2006.01)
*C07D 233/54* (2006.01)

(52) U.S. Cl. ............ 514/399; 548/341.5; 548/335.1

(58) Field of Classification Search ............ 514/399; 548/341.5, 335.1
See application file for complete search history.

(56) References Cited

U.S. PATENT DOCUMENTS

| | | | |
|---|---|---|---|
| 4,826,868 A | 5/1989 | Wachter et al. |
| 5,011,851 A | 4/1991 | Meanwell |
| 5,051,518 A | 9/1991 | Murray et al. |
| 5,164,381 A | 11/1992 | Wachter et al. |
| 5,717,100 A | 2/1998 | Selnick et al. |
| 5,965,583 A | 10/1999 | Beers et al. |
| 6,083,949 A | 7/2000 | Liverton et al. |

FOREIGN PATENT DOCUMENTS

| | | |
|---|---|---|
| EP | 0442448 A2 | 8/1991 |
| EP | 0293220 B1 | 8/1994 |
| WO | WO 9205148 | 4/1992 |
| WO | WO 9711704 | 4/1997 |
| WO | WO 9712876 | 4/1997 |
| WO | WO 9901449 | 1/1999 |
| WO | WO 0138324 A2 | 5/2001 |
| WO | WO 0166539 A1 | 9/2001 |
| WO | WO 01/85723 A1 | 11/2001 |
| WO | WO 0185724 A1 | 11/2001 |
| WO | WO 0190078 A1 | 11/2001 |
| WO | WO 04/07463 A1 | 1/2004 |

OTHER PUBLICATIONS

Peter et al. Digestive Disease 2006, 24, 70-82.*
Crawley, J.N. ESI Special Topics, Oct. 2001; http://www.esi-topics.com/schizophrenia/interviews/dr-jacqueline-n-crawley.html.*
de Tullio, P. et al. Therapeutic and Chemical Developments of Cholecystokinin Receptor Ligands. *Exp. Opin. Invest. Drugs* 2000, 9(1), 129-146.
Gigoux, V. et al. Arginine 336 and Asparagine 333 of the Human Cholecystokinin-A Receptor Binding Site Interact with the Penultimate Aspartic Acid and the C-Terminal Amide of Cholecystokinin. *J. Biol. Chem.* 1999, 274(29), 20457-20464.
Harper, E.A. et al. Analysis of Variation in L-365,260 Competition Curves in Radioligand Binding Assays. *Br. J. Pharmacol.* 1996, 118, 1717-1726.
Hull, R.A. et al. 2-Naphthalenesulphonyl L-aspartyl-(2-phenethyl)amide (2-NAP)—A Selective Cholecystokinin CCKA-Receptor Antagonist. *Br. J. Pharmacol.* 1993, 108, 734-740.
Klapars, A. et al. A General and Efficient Copper Catalyst for the Amidation of Aryl Halides and the N-Arylation of Nitrogen Heterocycles. *J. Am. Chem. Soc.* 2001, 123(31), 7727-7729.
Klausner, Y.S. and M. Bodzansky. The Azide Method in Peptide Synthesis: Its Scope and Limitations. *Synthesis* 1974, 8, 549-559.
Morton, M.F. et al. Pharmacological Comparison of the Alternatively Spliced Short and Long CCK2 Receptors. *Br. J. Pharmacol.* 2003, 140(1), 218-224.
Saito, T. et al. Total Synthesis of the Furaquinocins. *J. Am. Chem. Soc.* 1998, 120(45), 11633-11644.
Wang, Z. A New Synthesis for Methyl 2-Benzyloxyphenylacetate. *Synth. Commun.* 1999, 29(13), 2361-2364.
Wolfe, J.P. et al. Simple Efficient Catalyst System for the Palladium-Catalyzed Amination of Aryl Chlorides, Bromides, and Triflates. *J. Org. Chem.* 2000, 65(4), 1158-1174.
Laufer, S.A. et al. Imidazole Inhibitors of Cytokine Release: Probing Substituents in the 2 Position. *J. Med. Chem.* 2002, 45, 4695-4705.
Meanwell, N.A. et al. Nonprostanoid Prostacyclin Mimetics. 3. Structural Variations of the Diphenyl Heterocycle Moiety. *J. Med. Chem.* 1992, 35, 3498-3512.
International Search Report dated May 23, 2005, for corresponding international application PCT/US2004/043191.

* cited by examiner

*Primary Examiner*—Kamal A. Saeed
*Assistant Examiner*—Jason M. Nolan
(74) *Attorney, Agent, or Firm*—John Harbour

(57) ABSTRACT

Certain imidazole compounds are CCK1 modulators useful in the treatment of CCK1 mediated diseases.

30 Claims, No Drawings

CCK-1 RECEPTOR MODULATORS

This application claims priority to provisional application, which is U.S. Ser. No. 60/531,795 filed Dec. 22, 2003. The complete disclosures of the aforementioned related U.S. patent applications are hereby incorporated herein by reference for all purposes.

This invention relates to CCK-1 receptor modulators for the treatment of gastrointestinal and CNS disorders. More particularly, this invention relates to certain imidazole compounds useful as selective agonists or antagonists of the CCK-1 receptor.

BACKGROUND OF THE INVENTION

Cholecystokinin (CCK) is a brain-gut peptide hormone located both in the gastrointestinal system and in the central nervous system. The actions of CCK are mediated by two G-protein coupled receptors: CCK-1 (formerly CCK-A) and CCK-2 (formerly CCK-B/gastrin). These CCK receptors are expressed throughout the gastrointestinal system and in different parts of the central nervous system including the cortex, the striatum, the hypothalamus, the hippocampus, the olfactory bulb, the vagal afferent neurones, in different enteric nerves, and in the genital tract.

CCK has a number of biological actions. CCK is the primary hormonal regulator of gall bladder contraction in response to a meal. CCK stimulates pancreatic and biliary secretions and regulates GI motility and specifically gut and colonic motility. CCK promotes protein synthesis and cell growth, especially in the GI system and in the pancreas. CCK is involved in mediating satiety after a meal. CCK is an important neuromodulator and neurotransmitter involved in anxiety and panic disorder. CCK modulates the release of dopamine. CCK is also known to antagonize morphine and beta-endorphine induced analgesia and the action on nociception. A review of CCK receptors, ligands and the activities thereof may be found in P. de Tullio et al., Exp. Opin. Invest. Drugs 2000, 9(1):129-146.

A number of CCK-1 receptor antagonists are presently in clinical trials including, tarazepide, devazepide and lintitript. Phase III equivalent trials are in progress by Rotta Research Group and Forest Laboratories on dexloxiglumide, a CCK-1 antagonist for the treatment of constipation, irritable bowel syndrome and non-ulcer dyspepsia.

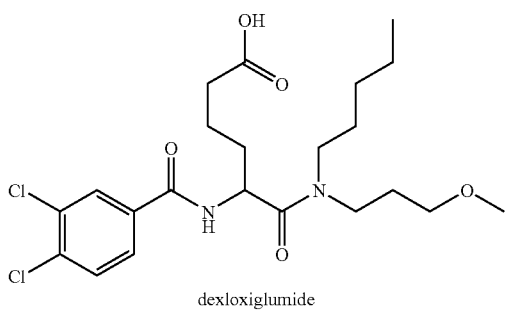

dexloxiglumide

Also, Kaken Pharmaceuticals and Mitsubishi-Tokyo Pharmaceuticals are awaiting registration in Japan on loxiglumide, a CCK-1 receptor antagonist for the treatment of GI cancers and pancreatitis. Loxiglumide is the racemate of dexloxiglumide.

A number of CCK-1 receptor agonists are under preclinical investigation. Glaxo Smith Kline, Inc. is investigating GW 5823, GW 7854, GW 7178 and GW 8573, 1,5-benzodiaepines for the treatment of gallstones, gastrointestinal disease and obesity.

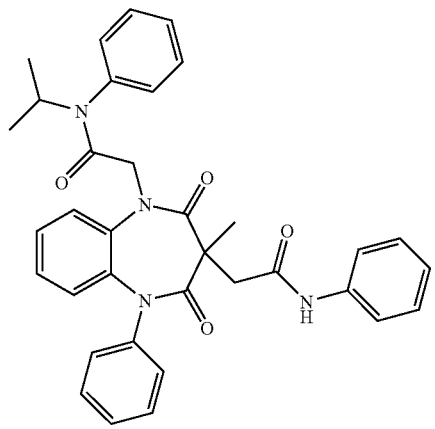

GW 7178

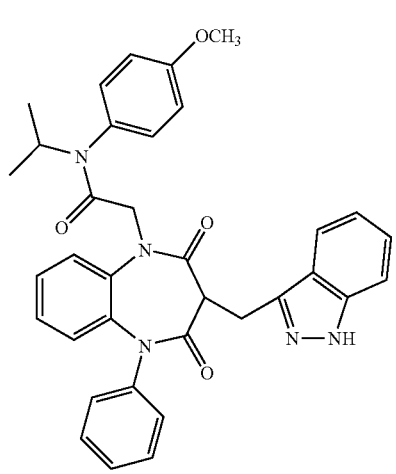

GW 5823

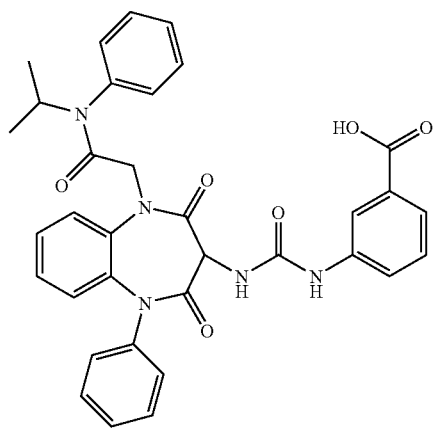

GW 7854

Also, Pfizer is investigating the CCK-1 receptor agonist, PD 170292, for obesity.

In Patent application WO 01/85723 there are disclosed certain imidazoles for the inhibition of gastrin and cholecystokinin receptor ligands of the general formula:

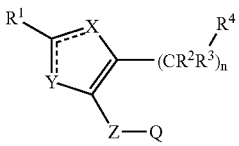

In Patent application WO 01/66539 there are disclosed certain imidazoles for the inhibition of raf kinases for the treatment of cancers of the general formula:

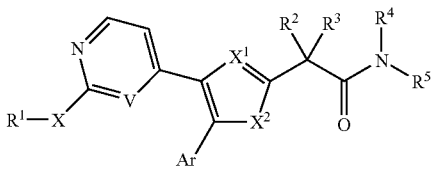

These compounds are not taught as inhibitors of CCK receptors.

Applicants have now discovered that certain imidazoles as described below are useful CCK-1 receptor modulators, agonists and antagonists, and most particularly antagonists. As such, these compounds are useful to treat a number of disease states mediated by CCK.

SUMMARY OF THE INVENTION

There is provided by the present invention a CCK-1 receptor modulator having the general formula:

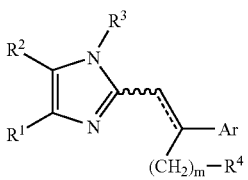

(I)

wherein, $R^1$ and $R^2$ can be the same or different and are selected from the group consisting of;

a) phenyl, optionally mono-, di- or tri-substituted with $R^p$ or di-substituted on adjacent carbons with —$OC_{1-4}$alkyleneO—, —$(CH_2)_{2-3}$NH—, —$(CH_2)_{1-2}$NH$(CH_2)$—, —$(CH_2)_{2-3}$N($C_{1-4}$alkyl)— or —$(CH_2)_{1-2}$N($C_{1-4}$alkyl)($CH_2$)—;

$R^p$ is selected from the group consisting of —OH, —$C_{1-6}$alkyl, —$OC_{1-6}$alkyl, phenyl, —Ophenyl, benzyl, —Obenzyl, —$C_{3-6}$cycloalkyl, —$OC_{3-6}$cycloalkyl, —CN, —$NO_2$, —N($R^y$)$R^z$ (wherein $R^y$ and $R^z$ are independently selected from —H, —$C_{1-6}$alkyl or —$C_{1-6}$alkenyl, or $R^y$ and $R^z$ may be taken together with the nitrogen of attachment to form an otherwise aliphatic hydrocarbon ring, said ring having 4 to 7 members, optionally having one carbon replaced with >O, =N—, >NH or >N($C_{1-4}$alkyl), optionally having one carbon substituted with —OH, and optionally having one or two double bonds in the ring), —(C=O)N($R^y$)$R^z$, —(N—$R^t$)COR$^t$, —(N—$R^t$)$SO_2C_{1-6}$alkyl (wherein $R^t$ is —H or —$C_{1-6}$alkyl or two $R^t$ in the same substituent may be taken together with the amide of attachment to form an otherwise aliphatic hydrocarbon ring, said ring having 4 to 6 members), —(C=O)$C_{1-6}$alkyl, —(S=(O)$_n$)—$C_{1-6}$alkyl (wherein n is selected from 0, 1 or 2), —$SO_2$N($R^y$)$R^z$, —$SCF_3$, halo, —$CF_3$, —$OCF_3$, —COOH and —$COOC_{1-6}$alkyl;

b) phenyl or pyridyl fused at two adjacent ring members to a three membered hydrocarbon moiety to form a fused five membered aromatic ring, which moiety has one carbon atom replaced by >O, >S, >NH or >N($C_{1-4}$alkyl) and which moiety has up to one additional carbon atom optionally replaced by N, the fused rings optionally mono-, di- or tri-substituted with $R^p$;

c) phenyl fused at two adjacent ring members to a four membered hydrocarbon moiety to form a fused six membered aromatic ring, which moiety has one or two carbon atoms replaced by N, the fused rings optionally mono-, di- or tri-substituted with $R^p$;

d) naphthyl, optionally mono-, di- or tri-substituted with $R^p$;

e) a monocyclic aromatic hydrocarbon group having five ring atoms, having a carbon atom which is the point of attachment, having one carbon atom replaced by >O, >S, >NH or >N($C_{1-4}$alkyl), having up to one additional carbon atoms optionally replaced by N, optionally mono- or di-substituted with $R^p$ and optionally benzo fused, where the benzo fused moiety is optionally mono-, di- or tri-substituted with $R^p$; and f) a monocyclic aromatic hydrocarbon group having six ring atoms, having a carbon atom which is the point of attachment, having one or two carbon atoms replaced by N, having one N optionally oxidized to the N-oxide, optionally mono- or di-substituted with $R^p$ and optionally benzo fused, where the benzo fused moiety is optionally mono- or di-substituted with $R^p$;

$R^3$ is selected from the group consisting of —H and —$C_{1-6}$alkyl;

m is selected from 0, 1, or 2;

Ar is selected from the group consisting of:

A) phenyl, optionally mono-, di- or tri-substituted with $R^r$ or di-substituted on adjacent carbons with —$OC_{1-4}$alkyleneO—, —$(CH_2)_{2-3}$NH—, —$(CH_2)_{1-2}$NH$(CH_2)$—, —$(CH_2)_{2-3}$N($C_{1-4}$alkyl)— or —$(CH_2)_{1-2}$N($C_{1-4}$alkyl)($CH_2$)—;

$R^r$ is selected from the group consisting of —OH, —$C_{1-6}$alkyl, —$OC_{1-6}$alkyl, phenyl, —Ophenyl, benzyl, —Obenzyl, —$C_{3-6}$cycloalkyl, —$OC_{3-6}$cycloalkyl, —CN, —$NO_2$, —N($R^a$)$R^b$ (wherein $R^a$ and $R^b$ are independently selected from —H, —$C_{1-6}$alkyl or —$C_{1-6}$alkenyl, or $R^a$ and $R^b$ may be taken together with the nitrogen of attachment to form an otherwise aliphatic hydrocarbon ring, said ring having 4 to 7 members, optionally having one carbon replaced with >O, =N—, >NH or >N($C_{1-4}$alkyl), optionally having one carbon substituted with —OH, and optionally having one or two double bonds in the ring), —(C=O)N($R^a$)$R^b$, —(N—$R^c$)COR$^c$, —(N—$R^c$)$SO_2C_{1-6}$alkyl (wherein $R^c$ is H or $C_{1-6}$alkyl or two $R^c$ in the same substituent may be taken together with the amide of attachment to form an otherwise aliphatic hydrocarbon ring, said ring having 4 to 6 members), —(C=O)$C_{1-6}$alkyl, —(S=(O)$_q$)—$C_{1-6}$alkyl (wherein q is selected from 0, 1 or 2), —$SO_2$N($R^a$)$R^b$, —$SCF_3$, halo, —$CF_3$, —$OCF_3$, and —$COOC_{1-6}$alkyl;

B) phenyl or pyridyl fused at two adjacent ring members to a three membered hydrocarbon moiety to form a fused five membered aromatic ring, which moiety has one carbon atom replaced by >O, >S, >NH or >N($C_{1-4}$ alkyl) and which moiety has up to one additional carbon atom optionally replaced by N, the fused rings optionally mono-, di- or tri-substituted with $R^r$;

C) phenyl fused at two adjacent ring members to a four membered hydrocarbon moiety to form a fused six membered aromatic ring, which moiety has one or two carbon atoms replaced by N, the fused rings optionally mono-, di- or tri-substituted with $R^r$;

D) naphthyl, optionally mono-, di- or tri-substituted with $R^r$;

E) a monocyclic aromatic hydrocarbon group having five ring atoms, having a carbon atom which is the point of attachment, having one carbon atom replaced by >O, >S, >NH or >N($C_{1-4}$alkyl), having up to one additional carbon atoms optionally replaced by N, optionally mono- or di-substituted with $R^r$ and optionally benzo fused on the condition that two or fewer of said carbon ring atoms are replaced by a heteroatom, where the benzo fused moiety is optionally mono-, di- or tri-substituted with $R^r$; and F) a monocyclic aromatic hydrocarbon group having six ring atoms, having a carbon atom which is the point of attachment, having one or two carbon atoms replaced by N, optionally mono- or di-substituted with $R^r$ and optionally benzo fused, where the benzo fused moiety is optionally mono- or di-substituted with $R^r$;

$R^4$ is selected from the group consisting of;

I) —$COOR^5$, where $R^5$ is selected from the group consisting of —H and —$C_{1-4}$alkyl, and II) —$CONR^6R^7$, where $R^6$ and $R^7$ are independently selected from the group consisting of —H, —$C_{1-6}$alkyl and —$C_{3-6}$cycloalkyl optionally hydroxy substituted, or $R^6$ and $R^7$ may be taken together with the nitrogen of attachment to form an otherwise aliphatic hydrocarbon ring, said ring having 5 to 7 members, optionally having one carbon replaced with >O, =N—, >NH or >N($C_{1-4}$alkyl) and optionally having one or two double bonds in the ring;

and enantiomers, diastereomers, hydrates, solvates and pharmaceutically acceptable salts, esters and amides thereof.

DETAILED DESCRIPTION OF THE INVENTION

Preferably $R^1$ and $R^2$, optionally substituted as described above, are selected from the group consisting of:

a) phenyl, 5-, 6-, 7-, 8-benzo-1,4-dioxanyl, 4-, 5-, 6-, 7-benzo-1,3-dioxolyl, 4-, 5-, 6-, 7-indolinyl, 4-, 5-, 6-, 7-isoindolinyl, 1,2,3,4-tetrahydro-quinolin-4, 5, 6 or 7-yl, 1,2,3,4-tetrahydro-isoquinolin-4, 5, 6 or 7-yl, b) 4-, 5-, 6- or 7-benzoxazolyl, 4-, 5-, 6- or 7-benzothiophenyl, 4-, 5-, 6- or 7-benzofuranyl, 4-, 5-, 6- or 7-indolyl, 4-, 5-, 6- or 7-benzthiazolyl, 4-, 5-, 6- or 7-benzimidazolyl, 4-, 5-, 6- or 7-indazolyl, imidazo[1,2-a]pyridin-5, 6, 7 or 8-yl, pyrazolo[1,5-a]pyridin-4, 5, 6 or 7-yl, 1H-pyrrolo[2,3-b]pyridin-4, 5 or 6-yl, 1H-pyrrolo[3,2-c]pyridin-4, 6 or 7-yl, 1H-pyrrolo[2,3-c]pyridin-4; 5 or 7-yl, 1H-pyrrolo[3,2-b]pyridin-5, 6 or 7-yl, c) 5-, 6-, 7- or 8-isoquinolinyl, 5-, 6-, 7- or 8-quinolinyl, 5-, 6-, 7- or 8-quinoxalinyl, 5-, 6-, 7- or 8-quinazolinyl, d) naphthyl, e) furanyl, oxazolyl, isoxazolyl, thiophenyl, thiazolyl, isothiazolyl, pyrrolyl, imidazolyl, pyrazolyl, 3-indoxazinyl, 2-benzoxazolyl, 2- or 3-benzothiophenyl, 2- or 3-benzofuranyl, 2- or 3-indolyl, 2-benzthiazolyl, 2-benzimidazolyl, or 3-indazolyl, f) pyridinyl, pyridinyl-N-oxide, pyrazinyl, pyrimidinyl, pyridazinyl, 1-, 3- or 4-isoquinolinyl, 2-, 3- or 4-quinolinyl, 2- or 3-quinoxalinyl, 2- or 4-quinazolinyl, and 1-oxy-pyridin-2, 3, or 4-yl.

Most preferably $R^1$ and $R^2$ can be the same or different and optionally substituted as described above, and are selected from the group consisting of phenyl, pyridinyl, and naphthyl. Specific $R^1$ and $R^2$ are selected from the group consisting of phenyl, 2-methoxy-phenyl, 3-methoxy-phenyl, 4-methoxy-phenyl, 2,3-dimethoxy-phenyl, 2,4-dimethoxy-phenyl, 3,4-dimethoxy-phenyl, 2-chloro-phenyl, 3-chloro-phenyl, 4-chloro-phenyl, 2,3-dichloro-phenyl, 2,4-dichloro-phenyl, 3,4-dichlorophenyl, 2,5-dichloro-phenyl, 2-fluoro-phenyl, 3-fluoro-phenyl, 4-fluoro-phenyl, 2-methyl-phenyl, 3-methyl-phenyl, 4-methyl-phenyl, 2,5-dimethyl-phenyl, 2-trifluoromethyl-phenyl, 3-trifluoromethyl-phenyl, 4-trifluoromethyl-phenyl, 3-trifluoromethoxy-phenyl, 4-trifluoromethoxy-phenyl, 4-t-butyl-phenyl, naphthalen-2-yl, naphthalen-1-yl, pyridin-2-yl, pyridin-3-yl, pyridin-4-yl, 4-methanesulfonyl-phenyl, 4-isopropyl-phenyl, 4-ethoxy-phenyl, 4-hydroxy-phenyl, benzo[1,3]diox-5-yl, and 2,3-dihydro benzo[1,4]dioxin-6-yl.

Preferably $R^p$ is selected from the group consisting of —OH, —$CH_3$, —$CH_2CH_3$, i-propyl, t-butyl, —$OCH_3$, —$OCH_2CH_3$, —$OCH(CH_3)_2$, phenyl, —Ophenyl, benzyl, —Obenzyl, cyclopropyl, cyclobutyl, cyclopentyl, cyclohexyl, —Ocyclopentyl, —Ocyclohexyl, —CN, —$NO_2$, —$NH_2$, —$NHCH_3$, —$NHCH_2CH_3$, —$NH(CH_2CH_2CH_3)$, —$NH(CH(CH_3)CH_2CH_3)$, —$NH(allyl)$, —$NH(CH_2(CH_3)_2)$, —$N(CH_3)_2$, —$N(CH_2CH_3)_2$, —$NCH_3(CH_2CH_2CH_3)$, —$NCH_3(CH_2CH_3)$, —$NCH_3(CH(CH_3)_2)$, pyrrolidin-2-on-1-yl, azetidinyl, piperidin-1-yl, 2- or 3-pyrrolin-1-yl, morpholin-4-yl, thiomorpholin-4-yl, piperazin-1-yl, pyrrolidin-1-yl, homopiperidin-1-yl, —$C(O)NH_2$, —$C(O)N(CH_3)_2$, —$C(O)NH(CH_3)$, —$NH(CO)H$, —NH-$COCH_3$, —$NCH_3(CO)H$, —$NCH_3COCH_3$, —$NHSO_2CH_3$, —$NCH_3SO_2CH_3$, —$C(O)CH_3$, —$SOCH_3$, —$SO_2CH_3$, —$SO_2NH_2$, —$SO_2NHCH_3$, —$SO_2N(CH_3)_2$, —$SCF_3$, —F, —Cl, —Br, —I, —$CF_3$, —$OCF_3$, —COOH, —$COOCH_3$, and —$COOCH_2CH_3$.

Most preferably $R^p$ is selected from the group consisting of —$CH_3$, —$OCH_3$, —$OCH_2CH_3$, —Cl, —F, —$CF_3$, —$OCF_3$, t-butyl, —$SO_2CH_3$, i-propyl and —OH.

Preferably $R^3$ is selected from the group consisting of —H, —$CH_3$, —$CH_2CH_3$, —$CH_2CH_2CH_3$, and —$CH(CH_3)_2$.

Most preferably $R^3$ is —H or —$CH_3$.

Preferably m is 0.

In one preferred embodiment of the invention, the Ar attached carbon is saturated and has the configuration

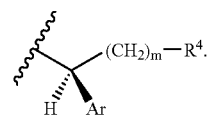

In one more preferred embodiment of the invention, the Ar attached carbon is saturated and has the configuration

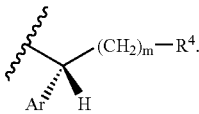

In another preferred embodiment of the present invention, the Ar attached carbon is unsaturated and has the configuration

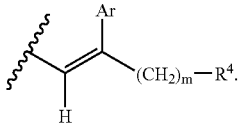

In another more preferred embodiment of the present invention, the Ar attached carbon is unsaturated and has the configuration

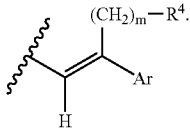

Preferably Ar, optionally substituted as described above, is selected from the group consisting of:
A) phenyl, 5-, 6-, 7-, 8-benzo-1,4-dioxanyl, 4-, 5-, 6-, 7-benzo-1,3-dioxolyl, 4-, 5-, 6-, 7-indolinyl, 4-, 5-, 6-, 7-isoindolinyl, 1,2,3,4-tetrahydro-quinolin-4, 5, 6 or 7-yl, 1,2,3,4-tetrahydro-isoquinolin-4, 5, 6 or 7-yl,
B) 4-, 5-, 6- or 7-benzoxazolyl, 4-, 5-, 6- or 7-benzothiophenyl, 4-, 5-, 6- or 7-benzofuranyl, 4-, 5-, 6- or 7-indolyl, 4-, 5-, 6- or 7-benzthiazolyl, 4-, 5-, 6- or 7-benzimidazolyl, 4-, 5-, 6- or 7-indazolyl, imidazo[1,2-a]pyridin-5, 6, 7 or 8-yl, pyrazolo[1,5-a]pyridin-4, 5, 6 or 7-yl, 1H-pyrrolo[2,3-b]pyridin-4, 5 or 6-yl, 1H-pyrrolo[3,2-c]pyridin-4, 6 or 7-yl, 1H-pyrrolo[2,3-c]pyridin-4, 5 or 7-yl, 1H-pyrrolo[3,2-b]pyridin-5, 6 or 7-yl,
C) 5-, 6-, 7- or 8-isoquinolinyl, 5-, 6-, 7- or 8-quinolinyl, 5-, 6-, 7- or 8-quinoxalinyl, 5-, 6-, 7- or 8-quinazolinyl,
D) naphthyl,
E) furanyl, oxazolyl, isoxazolyl, thiophenyl, thiazolyl, isothiazolyl, pyrrolyl, imidazolyl, pyrazolyl, 3-indoxazinyl, 2-benzoxazolyl, 2- or 3-benzothiophenyl, 2- or 3-benzofuranyl, 2- or 3-indolyl, 2-benzthiazolyl, 2-benzimidazolyl, or 3-indazolyl,
F) pyridinyl, pyrazinyl, pyrimidinyl, pyridazinyl, 1-, 3- or 4-isoquinolinyl, 2-, 3- or 4-quinolinyl, 2- or 3-quinoxalinyl, 2- or 4-quinazolinyl.

More preferably Ar, optionally substituted as described above, is selected from the group consisting of phenyl, naphthyl, benzofuran-3-yl, 4-, 5-, 6- or 7-benzothiophenyl, 4-, 5-, 6- or 7-benzo[1,3]dioxolyl, 8-quinolinyl, 2-indolyl, 3-indolyl and pyridinyl. Most preferably Ar, optionally substituted as described above, is phenyl or naphthyl. Specific Ar are selected from the group consisting of phenyl, 2-methyl-phenyl, 3-methyl-phenyl, 4-methyl-phenyl, 2,5-dimethyl-phenyl, 2-trifluoromethyl-phenyl, 3-trifluoromethyl-phenyl, 4-trifluoromethyl-phenyl, 2-fluoro-3-trifluoromethyl-phenyl, 2-fluoro-phenyl, 3-fluoro-phenyl, 4-fluoro-phenyl, 2,3-difluoro-phenyl, 2-chloro-phenyl, 3-chloro-phenyl, 4-chloro-phenyl, 2,3-dichloro-phenyl, 3,4-dichlorophenyl, 2,6-dichlorophenyl, 3-iodo-phenyl, 2-chloro-4-fluoro-phenyl, benzofuran-3-yl, 2-methoxy-phenyl, 3-methoxy-phenyl, 4-methoxy-phenyl, 2,3-dimethoxyphenyl, 3-trifluoromethoxy-phenyl, 4-trifluoromethoxyphenyl, 3-ethoxy-phenyl, 3-trifluoromethylsulfanyl-phenyl, naphthalen-1-yl, naphthalen-2-yl, benzo[b]thiophen-4-yl, 3-nitro-phenyl, benzo[1,3]dioxol-5-yl, pyridin-3-yl, pyridin-4-yl, 3-indolyl, 1-methyl-indol-3-yl, 4-biphenyl, 3,5-dimethyl-phenyl, 3-isopropoxy-phenyl, 3-dimethylamino-phenyl, 2-flouro-5-methyl-phenyl, and 2-methyl-3-trifluoromethyl-phenyl. Preferably, there are 0, 1 or 2 $R^r$ substituents.

Preferably $R^r$ is selected from the group consisting of —OH, —CH$_3$, —CH$_2$CH$_3$, -propyl, -t-butyl, —OCH$_3$, —OCH$_2$CH$_3$, —OCH(CH$_3$)$_2$, phenyl, —Ophenyl, benzyl, —Obenzyl, cyclopentyl, cyclohexyl, —Ocyclopentyl, —Ocyclohexyl, —CN, —NO$_2$, —NH$_2$, —N(CH$_3$)$_2$, —N(CH$_2$CH$_3$)$_2$, pyrrolidin-2-on-1-yl, piperidin-1-yl, 2- or 3-pyrrolin-1-yl, morpholin-4-yl, thiomorpholin-4-yl, piperazin-1-yl, pyrrolidin-1-yl, —C(O)NH$_2$, —C(O)N(CH$_3$)$_2$, —C(O)NH(CH$_3$), —NHCOCH$_3$, —NHSO$_2$CH$_3$, —C(O)CH$_3$, —SOCH$_3$, —SO$_2$CH$_3$, —SO$_2$N(CH$_3$)$_2$, —SCF$_3$, —F, —Cl, —Br, —I, —CF$_3$, —COOCH$_3$.

Most preferably $R^r$ is selected from the group consisting of —CH$_3$, —OCH$_3$, —OCH$_2$CH$_3$, —OCH(CH$_3$)$_2$, —F, —Cl, —Br, —CF$_3$, and —OCF$_3$.

Preferably $R^4$ is selected from the group consisting of:
I) —COOH, —COOCH$_3$, —COOCH$_2$CH$_3$,
II) —CONH(CH$_3$), —CONH(CH$_2$CH$_3$), —CONH(CH$_2$CH$_2$CH$_3$), —CONH(CH(CH$_3$)$_2$), —CONH(CH$_2$CH$_2$CH$_2$CH$_3$), —CONH(CH(CH$_3$)CH$_2$CH$_3$), —CONH(C(CH$_3$)$_3$), —CONH(cyclohexyl), —CONH(2-hydroxy-cyclohexyl), —CON(CH$_3$)$_2$, —CONCH$_3$(CH$_2$CH$_3$), —CONCH$_3$(CH$_2$CH$_2$CH$_3$), —CONCH$_3$(CH(CH$_3$)$_2$), —CONCH$_3$(CH$_2$CH$_2$CH$_2$CH$_3$), —CONCH$_3$(CH(CH$_3$)CH$_2$CH$_3$), —CONCH$_3$(C(CH$_3$)$_3$), —CON(CH$_2$CH$_3$)$_2$, —CO-piperidin-1-yl, —CO-morpholin-4-yl, —CO-piperazin-1-yl, —CO-pyrrolidin-1-yl, —CO-2-pyrrolin-1-yl, —CO-3-pyrrolin-1-yl, and —CO-piperidin-1-yl.

Most preferably $R^4$ is —COOH.

Preferred compounds have demonstrated CCK-1 agonist or antagonist activity, and are selected from the group consisting of:

EX Compound
1 (Z)-3-[5-Benzo[1,3]dioxol-5-yl-4-(2,5-dichloro-phenyl)-1H-imidazol-2-yl]-2-(3-chloro-phenyl)-acrylic acid;
2 (E)-3-[5-Benzo[1,3]dioxol-5-yl-4-(2,5-dichloro-phenyl)-1H-imidazol-2-yl]-2-(3-chloro-phenyl)-acrylic acid;
3 (Z)-3-[5-Benzo[1,3]dioxol-5-yl-4-(2,5-dichloro-phenyl)-1H-imidazol-2-yl]-2-m-tolyl-acrylic acid;
4 (Z)-3-[5-Benzo[1,3]dioxol-5-yl-4-(2,5-dichloro-phenyl)-1H-imidazol-2-yl]-2-naphthalen-1-yl-acrylic acid;
5 (Z)-3-[5-Benzo[1,3]dioxol-5-yl-4-(2,5-dichloro-phenyl)-1H-imidazol-2-yl]-2-(4-chloro-phenyl)-acrylic acid;
6 (Z)-3-[5-Benzo[1,3]dioxol-5-yl-4-(2,5-dichloro-phenyl)-1H-imidazol-2-yl]-2-p-tolyl-acrylic acid;
7 (Z)-3-[5-Benzo[1,3]dioxol-5-yl-4-(2,5-dichloro-phenyl)-1H-imidazol-2-yl]-2-(3-trifluoromethyl-phenyl)-acrylic acid;
8 (Z)-2-(3-Chloro-phenyl)-3-[4-(3,4-dichloro-phenyl)-5-(4-methoxy-phenyl)-1H-imidazol-2-yl]-acrylic acid;

9  (Z)-3-[4-(3,4-Dichloro-phenyl)-5-(4-methoxy-phenyl)-1H-imidazol-2-yl]-2-m-tolyl-acrylic acid;
10 (Z)-3-[4-(3,4-Dichloro-phenyl)-5-(4-methoxy-phenyl)-1H-imidazol-2-yl]-2-(3-trifluoromethyl-phenyl)-acrylic acid;
11 (Z)-3-[4-(3,4-Dichloro-phenyl)-5-(4-methoxy-phenyl)-1H-imidazol-2-yl]-2-p-tolyl-acrylic acid;
12 (Z)-2-(3-Chloro-phenyl)-3-(5-naphthalen-2-yl-4-pyridin-2-yl-1H-imidazol-2-yl)-acrylic acid;
13 (E)-3-[4-(3,4-Dichloro-phenyl)-5-(4-methoxy-phenyl)-1H-imidazol-2-yl]-2-naphthalen-1-yl-acrylic acid;
14 (E)-3-[4-(3,4-Dichloro-phenyl)-5-(4-methoxy-phenyl)-1H-imidazol-2-yl]-2-p-tolyl-acrylic acid;
15 (E)-2-(4-Chloro-phenyl)-3-[4-(3,4-dichloro-phenyl)-5-(4-methoxy-phenyl)-1H-imidazol-2-yl]-acrylic acid;
16 (E)-3-[4-(3,4-Dichloro-phenyl)-5-(4-methoxy-phenyl)-1H-imidazol-2-yl]-2-(3-trifluoromethyl-phenyl)-acrylic acid;
17 (E)-3-[4-(3,4-Dichloro-phenyl)-5-(4-methoxy-phenyl)-1H-imidazol-2-yl]-2-m-tolyl-acrylic acid;
18 (E)-2-(3-Chloro-phenyl)-3-[4-(3,4-dichloro-phenyl)-5-(4-methoxy-phenyl)-1H-imidazol-2-yl]-acrylic acid;
19 (E)-3-[5-Benzo[1,3]dioxol-5-yl-4-(2,5-dichloro-phenyl)-1H-imidazol-2-yl]-2-m-tolyl-acrylic acid;
20 (E)-3-[5-Benzo[1,3]dioxol-5-yl-4-(2,5-dichloro-phenyl)-1H-imidazol-2-yl]-2-(4-chloro-phenyl)-acrylic acid;
21 (E)-3-[5-Benzo[1,3]dioxol-5-yl-4-(2,5-dichloro-phenyl)-1H-imidazol-2-yl]-2-(3-trifluoromethyl-phenyl)-acrylic acid;
22 (E)-3-[5-Benzo[1,3]dioxol-5-yl-4-(2,5-dichloro-phenyl)-1H-imidazol-2-yl]-2-p-tolyl-acrylic acid;
23 (E)-3-[5-Benzo[1,3]dioxol-5-yl-4-(2,5-dichloro-phenyl)-1H-imidazol-2-yl]-2-naphthalen-1-yl-acrylic acid;
24 3-[4-(3,4-Dichloro-phenyl)-5-(4-methoxy-phenyl)-1H-imidazol-2-yl]-2-m-tolyl-propionic acid;
25 2-(3-Chloro-phenyl)-3-[4-(3,4-dichloro-phenyl)-5-(4-methoxy-phenyl)-1H-imidazol-2-yl]-propionic acid;
26 3-[4-(3,4-Dichloro-phenyl)-5-(4-methoxy-phenyl)-1H-imidazol-2-yl]-2-naphthalen-1-yl-propionic acid;
27 3-[4-(3,4-Dichloro-phenyl)-5-(4-methoxy-phenyl)-1H-imidazol-2-yl]-2-(3-trifluoromethyl-phenyl)-propionic acid;
28 2-(4-Chloro-phenyl)-3-[4-(3,4-dichloro-phenyl)-5-(4-methoxy-phenyl)-1H-imidazol-2-yl]-propionic acid;
29 3-[4-(3,4-Dichloro-phenyl)-5-(4-methoxy-phenyl)-1H-imidazol-2-yl]-2-p-tolyl-propionic acid;
30 3-(4,5-Di-p-tolyl-1H-imidazol-2-yl)-2-m-tolyl-propionic acid;
31 3-(1-Methyl-4,5-di-p-tolyl-1H-imidazol-2-yl)-2-m-tolyl-propionic acid;
32 3-[4,5-Bis-(2-chloro-phenyl)-1H-imidazol-2-yl]-2-naphthalen-1-yl-propionic acid;
33 3-[4,5-Bis-(3-methoxy-phenyl)-1H-imidazol-2-yl]-2-naphthalen-1-yl-propionic acid;
34 3-[4,5-Bis-(4-fluoro-phenyl)-1H-imidazol-2-yl]-2-naphthalen-1-yl-propionic acid; and
35 (Z)-3-[5-Benzo[1,3]dioxol-5-yl-4-(2,5-dichloro-phenyl)-1H-imidazol-2-yl]-2-(3-chloro-phenyl)-acrylic acid, sodium salt.

Pharmaceutically acceptable salts, esters, and amides include carboxylate salts (e.g., $C_{1-8}$alkyl, $C_{3-8}$cycloalkyl, aryl, $C_{2-10}$heteroaryl, or $C_{2-10}$ non-aromatic heterocyclic), amino addition salts, acid addition salts, esters, and amides that are within a reasonable benefit/risk ratio, pharmacologically effective and suitable for contact with the tissues of patients without undue toxicity, irritation, or allergic response. Representative salts for compounds of formula (I) displaying basic functionality include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. Representative addition salts for compounds of formula (I) displaying acidic functionality are those that form non-toxic base salts with such compounds. These salts may include alkali metal and alkali earth cations such as sodium, potassium, calcium, and magnesium, as well as non-toxic ammonium, quaternary ammonium, and amine cations such as tetramethyl ammonium, methylammonium, trimethylammonium, and ethylammonium. See example, S. M. Berge, et al., "Pharmaceutical Salts," J. Pharm. Sci., 1977, 66:1-19, which is incorporated herein by reference. Examples of suitable salts include (Z)-3-[5-benzo[1,3]dioxol-5-yl-4-(2,5-dichloro-phenyl)-1H-imidazol-2-yl]-2-(3-chloro-phenyl)-acrylic acid, sodium salt.

Representative pharmaceutically acceptable amides of the invention include those derived from ammonia, primary $C_{1-6}$ alkyl amines and secondary di($C_{1-6}$alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$alkyl primary amines, and di($C_{1-2}$alkyl)amines. Representative pharmaceutically acceptable esters of the invention include $C_{1-7}$alkyl, $C_{5-7}$cycloalkyl, phenyl, and phenyl($C_{1-6}$)alkyl esters. Preferred esters include methyl esters.

The features and advantages of the invention are apparent to one of ordinary skill in the art. Based on this disclosure, including the summary, detailed description, background, examples, and claims, one of ordinary skill in the art will be able to make modifications and adaptations to various conditions and usages. Publications described herein are incorporated by reference in their entirety.

The compounds as described above may be made according to processes within the skill of the art and/or that are described in the schemes and examples that follow. To obtain the various compounds herein, starting materials may be employed that carry the ultimately desired substituents though the reaction scheme with or without protection as appropriate. Alternatively, it may be necessary to employ, in the place of the ultimately desired substituent, a suitable group that may be carried through the reaction scheme and replaced as appropriate with the desired substituent.

The compounds as described above may be made according to Schemes A-F below. Persons skilled in the art will recognize that certain compounds are more advantageously produced by one scheme as compared to the other.

SCHEME A

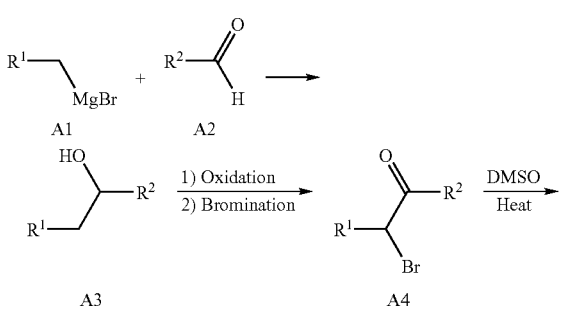

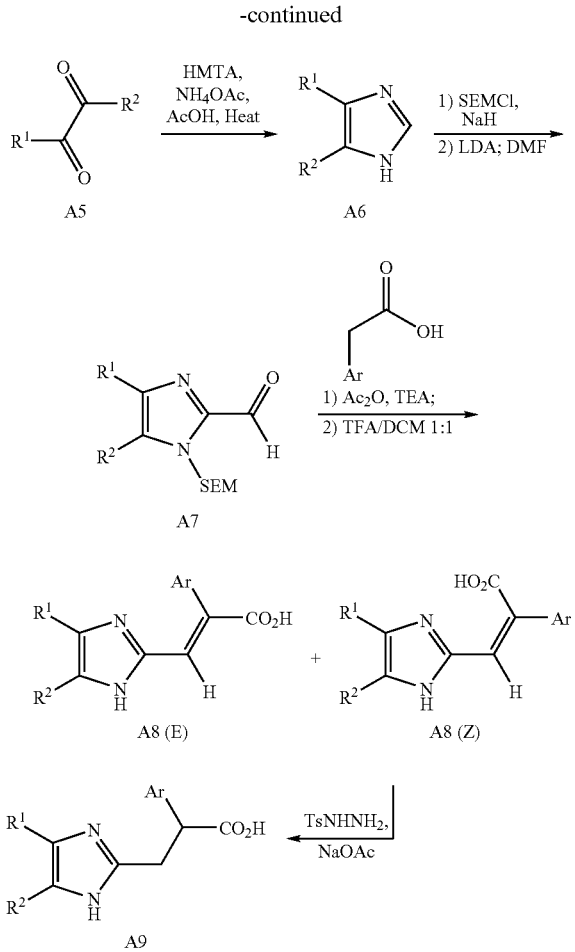

synthesis of imidazole A6 using HMTA (hexamethylenetetramine) can also be accomplished with formaldehyde and NH₄OAc. The protection (SEM) of imidazole A6 can also be accomplished with alternate protecting groups such as MEM, MOM, or benzyl. Arylacetic acids used to make A8 can be obtained from commercial sources or made by methods described by Z. Wang et al. (Synth. Commun. 1999, 29:2361-2364), or T. Saito et al. (J. Am. Chem. Soc. 1998, 120:11633-11644). The condensation of A7 with arylacetic acids results in a mixture of olefin isomers A8 (E) and A8 (Z). These isomers can typically be separated and isolated using chromatographic methods. Additionally, pure isomers A8 (E) and A8 (Z) can be isomerized to mixtures using photolysis and further separated by chromatographic methods. Reduction of A8 to A9 can be accomplished using TsNHNH₂ to produce a racemic mixture of acid A9. This mixture of optical isomers can be separated by chiral chromatographic methods. Alternatively, the reduction can be accomplished using catalytic hydrogenation methods or transfer hydrogenation methods.

SCHEME B

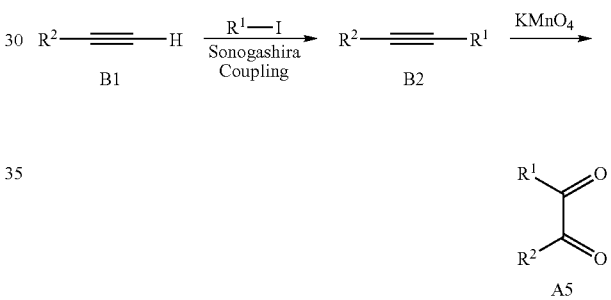

Referring to Scheme A, there are disclosed the following notes and additions. The Grignard reagent A1 can be purchased or synthesized from the corresponding arylmethyl bromide. Certain substituents on R¹ that are incompatible with the reaction conditions required to form A1 may require protection. Oxidation of alcohol A3 can be accomplished using a variety of conditions including Dess-Martin oxidation or Swern oxidation conditions. Diketone A5 can optionally be obtained by the method described in Scheme B or the diketone can be obtained from commercial sources. The Referring to Scheme B, there are disclosed the following notes and additions. Scheme B shows an alternative to the synthesis of diketone A5, which is then used in Scheme A to synthesize the desired products. Alkyne B1 can be obtained from commercial sources or synthesized by standard synthetic methods, such as coupling of trimethylsilylacetylene with an aryl bromide or iodide using a Sonogashira reaction, or by homologation of an aryl aldehyde using (EtO)₂P(O)C(N₂)C(O)CH₃.

SCHEME C

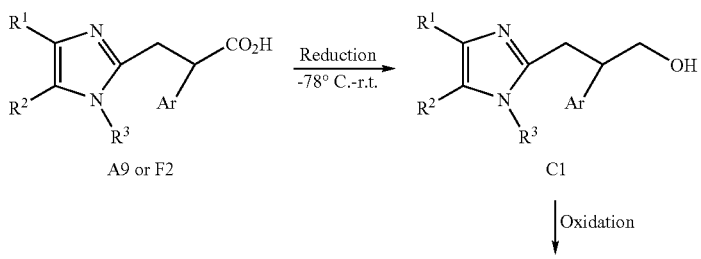

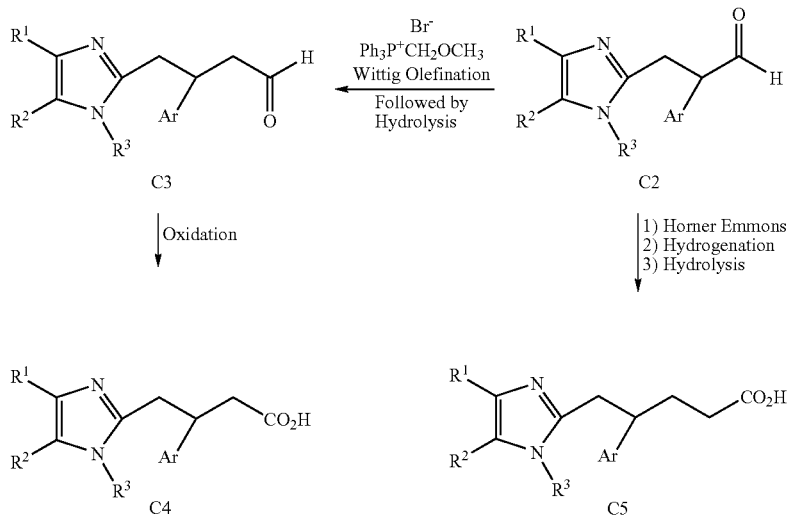

Referring to Scheme C, there are disclosed the following notes and additions. The starting acid can come from A9, F2, or when appropriate the imidazole can be protected at the $R^3$ position with a protecting group such as SEM. Of course, analogous acid A8 can be used to produce analogous C4 or C5. The reduction to C1 may be effected with a number of reducing agents including DIBAL-H and LAH. The oxidation reaction producing C2 may be carried out using Swern or Dess-Martin conditions. One carbon homologation to C3 is accomplished by a Wittig reaction using (methoxymethyl)triphenyl-phosphonium bromide and base, followed by oxidation to the acid C4. Alternatively the two carbon homologated acids C5 can be obtained by Horner-Emmons reaction, using $(EtO)_2P(O)CH_2CO_2Et$ to provide the acrylate, followed by reduction of the double bond by hydrogenation, and hydrolysis of the ester using a base such as LiOH.

SCHEME D

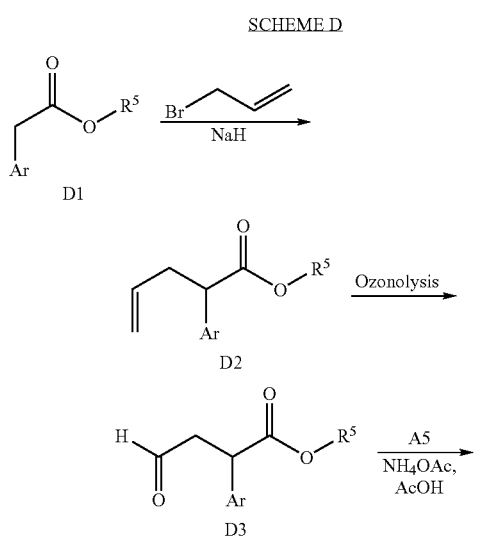

Referring to Scheme D, there are disclosed the following notes and additions. Ester D1 can be obtained from commercial sources or synthesized using methods described by Z. Wang et al. (Synth. Commun. 1999, 29:2361-2364) or T. Saito et al. (J. Am. Chem. Soc. 1998,120:11633-11644). Ester D2 can be prepared through deprotonation and reaction with allyl bromide. The olefin in D2 can be cleaved under ozonolysis conditions or with an osmium tetroxide/sodium periodate protocol to provide aldehyde D3. Condensation of the aldehyde D3 with benzoin A5 then affords esters of type D4. Hydrolysis with LiOH or another suitable base then affords the acid A9.

SCHEME E

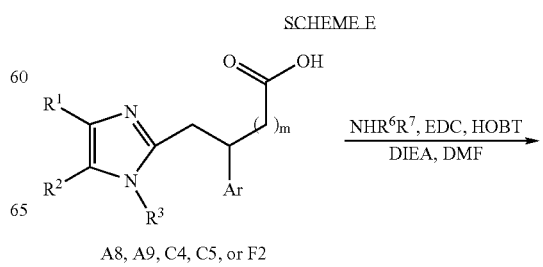

A8, A9, C4, C5, or F2

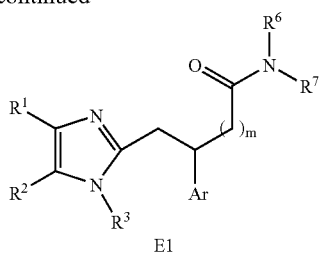

Referring to Scheme E, there are disclosed the following notes and additions. As shown, any of the acids A9, C4, C5, or F2, can be employed as a starting material. Of course, analogous acid A8 can be used to produce analogous E1. Alternatively, ester D4 might also be employed where $Me_3Al$ is used as a Lewis Acid with $NHR^6R^7$. Amines can be obtained from commercial sources or synthesized by known synthetic methods. Additionally, the amide bond formation can be accomplished by any number of known peptide coupling methods including DIC/DMAP or DCC. In some cases protection of the imidazole at the $R^3$ position with SEM or some other protecting group may be required.

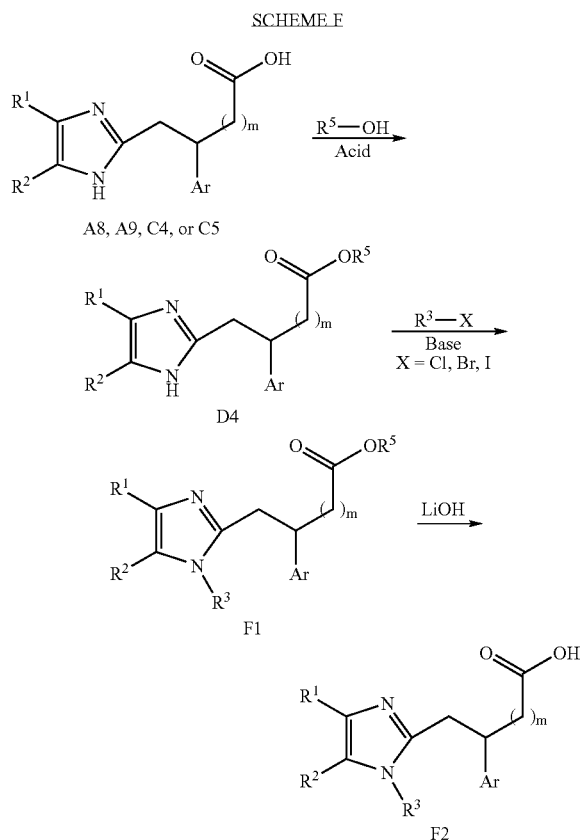

Referring to Scheme F, there are disclosed the following notes and additions. The starting ester D4 may be used, or alternatively esters obtained from acids A9, C4, or C5 may also be used to obtain the corresponding N-alkylated compounds F1. Of course, analogous acid A8 can be used to produce analogous F1 or F2. Alkyl halides would preferably be commercial or synthesized bromides or iodides, but in some cases alkyl chlorides could be used. Hydrolysis of ester F1 can be accomplished as described in Scheme D to provide the desired acid F2.

Compounds of the present invention may be administered in pharmaceutical compositions to treat patients (humans and other mammals) with disorders mediated by the CCK-1 receptor. As CCK-1 receptor modulators, the compounds may be divided into compounds that are pure or partial agonists and compounds that are antagonists or inverse agonists. Where the compound is a CCK-1 receptor antagonist or inverse agonist, it may be used in the treatment of pain, drug dependence, anxiety, panic attack, schizophrenia, pancreatic disorder, secretory disorder, gastrointestinal motility disorders, functional bowel disease, biliary colic, anorexia and cancer. Where the compound is a CCK-1 receptor agonist, it may be used in the treatment of obesity, hypervigilance and gallstones.

The pharmaceutical compositions can be prepared using conventional pharmaceutical excipients and compounding techniques known to those skilled in the art of preparing dosage forms. It is anticipated that the compounds of the invention can be administered by oral, parenteral, rectal, topical, or ocular routes or by inhalation. Preparations may also be designed to give slow release of the active ingredient. The preparation may be in the form of tablets, capsules, sachets, vials, powders, granules, lozenges, powders for reconstitution, liquid preparations, or suppositories. Preferably, compounds may be administered by intravenous infusion or topical administration, but more preferably by oral administration.

For oral administration, the compounds of the invention can be provided in the form of tablets or capsules, or as a solution, emulsion, or suspension. Tablets for oral use may include the active ingredient mixed with pharmaceutically acceptable excipients such as inert diluents, disintegrating agents, binding agents, lubricating agents, sweetening agents, flavoring agents, coloring agents and preservatives agents. Suitable inert fillers include sodium and calcium carbonate, sodium and calcium phosphate, lactose, starch, sugar, glucose, methyl cellulose, magnesium stearate, mannitol, sorbitol, and the like; typical liquid oral excipients include ethanol, glycerol, water and the like. Starch, polyvinyl-pyrrolidone, sodium starch glycolate, microcrystalline cellulose, and alginic acid are suitable disintegrating agents. Binding agents may include starch and gelatin. The lubricating agent, if present, will generally be magnesium stearate, stearic acid or talc. If desired, the tablets may be coated with a material such as glyceryl monostearate or glyceryl distearate to delay absorption in the gastrointestinal tract, or may be ,coated with an enteric coating. Capsules for oral use include hard gelatin capsules in which the active ingredient is mixed with a solid, semi-solid, or liquid diluent, and soft gelatin capsules wherein the active ingredient is mixed with water, an oil such as peanut oil or olive oil, liquid paraffin, a mixture of mono and di-glycerides of short chain fatty acids, polyethylene glycol 400, or propylene glycol.

Liquids for oral administration may be suspensions, solutions, emulsions or syrups or may be presented as a dry product for reconstitution with water or other suitable vehicles before use. Compositions of such liquid may contain pharmaceutically-acceptable excipients such as suspending agents (for example, sorbitol, methyl cellulose, sodium alginate, gelatin, hydroxyethylcellulose, carboxymethylcellulose, aluminium stearate gel and the like); non-aqueous vehicles, which include oils (for example, almond oil or fractionated coconut oil), propylene glycol, ethyl alcohol or water; preservatives (for example, methyl or propyl p-hydroxybenzoate or sorbic acid); wetting agents such as lecithin; and, if needed, flavoring or coloring agents.

The compounds of this invention may also be administered by non-oral routes. The compositions may be formulated for rectal administration as a suppository. For parenteral use, including intravenous, intramuscular, intraperitoneal, or subcutaneous routes, the compounds of the invention will generally be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit dose form such as ampules or disposable injection devices, in multi-dose forms such as vials from which the appropriate dose may be withdrawn, or in a solid form or pre-concentrate that can be used to prepare an injectable formulation. Another mode of administration of the compounds of the invention may utilize a patch formulation to affect transdermal delivery. The compounds of this invention may also be administered by inhalation, via the nasal or oral routes using a spray formulation consisting of the compound of the invention and a suitable carrier.

Effective doses of the compounds of the present invention may be ascertained by conventional methods. The specific dosage level required for any particular patient will depend on a number of factors, including severity of the condition being treated, the route of administration, and the weight of the patient. Oral doses range from about 0.05 to 200 mg/kg, daily, taken in 1 to 4 separate doses. Some compounds of the invention may be orally dosed in the range of about 0.05 to about 50 mg/kg daily, others may be dosed at 0.05 to about 20 mg/kg daily, while still others may be dosed at 0.1 to about 10 mg/kg daily. Infusion doses can range from about 1 to 1000 μg/kg/min of inhibitor, admixed with a pharmaceutical carrier over a period ranging from several minutes to several days. For topical administration compounds of the present invention may be mixed with a pharmaceutical carrier at a concentration of about 0.1% to about 10% of drug to vehicle.

EXAMPLES

NMR spectra were obtained on either a Bruker model DPX400 (400 MHz) or DPX500 (500 MHz) spectrometer. The format of the $^1$H NMR data below is: chemical shift in ppm down field of the tetramethylsilane reference (multiplicity, coupling constant J in Hz, integration).

Mass spectra were obtained on an Agilent series 1100 MSD using electrospray ionization (ESI) in either positive or negative mode as indicated. The "mass calculated" for a molecular formula is the monoisotopic mass of the compound.

Protocols for Reversed-Phase HPLC

Reversed-Phase HPLC was performed on a Hewlett Packard (Agilent) 1100 at room temperature using the methods described below. Retention times are reported in minutes.

Method A
Column: Xterra™, RP18, 3.5 μm, 4.6×50 mm
Mobile Phase: Acetonitrile/Water with 0.1% TFA
Flow rate: 1.5 mL/min
Detection wavelength: 220 & 254 nm

| Gradient (Acetonitrile/Water): | | |
| --- | --- | --- |
| 1) | 0.0 min | 1.0% Acetonitrile |
| 2) | 3.5 min | 85% Acetonitrile |
| 3) | 5 min | 85% Acetonitrile |

Method B
Column: XTerra Prep MS C18, 5 μm, 19×50 mm
Mobile Phase: Acetonitrile/Water with 0.1% TFA
Flow rate: 25 mL/min
Detection wavelength: 220 & 254 nm

| Gradient: | | |
| --- | --- | --- |
| 1) | 0.0 min | 15% Acetonitrile |
| 2) | 13.0 min | 99% Acetonitrile |
| 3) | 15.0 min | 99% Acetonitrile |

Method C
Column: Zorbax Eclipse XDB-C8, 5 μm, 4.6×150 mm
Mobile Phase: Acetonitrile/Water with 0.1% TFA
Flow rate: 0.75 mL/min
Detection wavelength: 220 & 254 nm

| Gradient (Acetonitrile/Water): | | |
| --- | --- | --- |
| 1) | 0.0 min | 1% Acetonitrile |
| 2) | 8.0 min | 99% Acetonitrile |
| 3) | 12.0 min | 99% Acetonitrile |

Method D
Column: Chromolith SpeedROD, RP18e, 4.6×50 mm
Mobile Phase: Acetonitrile/Water with 0.1% TFA
Flow rate: 5.0 mL/min
Detection wavelength: 220 & 254 nm

| Gradient (Acetonitrile/Water): | | |
| --- | --- | --- |
| 1) | 0.0 min | 1.0% Acetonitrile |
| 2) | 2.0 min | 85% Acetonitrile |
| 3) | 3.0 min | 85% Acetonitrile |

Normal-phase Column Chromatography

Normal-phase column chromatography was accomplished using ISCO Foxy 200 or ISCO OPTIX 10× systems employing one of the following commercially available prepacked columns: Biotage 40S ($SiO_2$ 40 g), Biotage 40M ($SiO_2$ 90 g), Biotage 40L ($SiO_2$ 120 g), Biotage 65M ($SiO_2$ 300 g) or ISCO Redisep ($SiO_2$, 10 g, 12 g, 35 g, 40 g, or 120 g).

Example 1

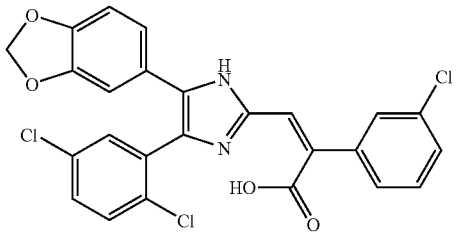

(Z)-3-[5-Benzo[1,3]dioxol-5-yl-4-(2,5-dichloro-phenyl)-1H-imidazol-2-yl]-2-(3-chloro-phenyl)-acrylic acid.

The title compound was prepared as described in Scheme A using the following procedure.

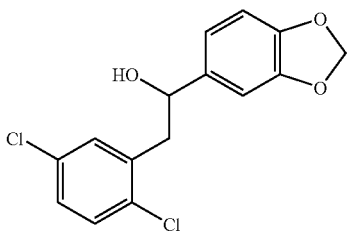

A. 1-Benzo[1,3]dioxol-5-yl-2-(2,5-dichloro-Phenyl)-ethanol. To a stirred 0.5 M solution of (2,5-dichloro-benzyl)-magnesium bromide in THF (500 mL, 250 mmol) under $N_2$ at 0° C. was added benzo[1,3]dioxole-5-carbaldehyde (17.0 g, 113.0 mmol) in small portions. The reaction mixture was allowed to warm to room temperature (rt) and was stirred for 1 h. The mixture was diluted with 1 N HCl (200 mL) and EtOAc (200 mL). The layers were separated, and the organic layer was washed with brine, dried ($Na_2SO_4$) and concentrated under reduced pressure. The crude solid was recrystallized from $Et_2O$/hexane to give 24.8 g (69%) of a white solid. HPLC: $R_t$=1.35 (Method D). $^1$H NMR (500 MHz, $CDCl_3$): 7.30 (d, J=8.5 Hz, 1H), 7.22 (d, J=2.5 Hz, 1H), 7.16 (dd, J=8.5, 2.7 Hz, 1H), 6.91 (d, J=1.4 Hz, 1H), 6.80 (dd, J=8.0, 1.6 Hz, 1H), 6.77 (d, J=8.0 Hz, 1H), 5.97 (q, J=2.5, 1.4 Hz, 2H), 4.93-4.89 (m, 1H), 3.10 (dd, J=13.7, 4.4 Hz, 1H), 3.01 (dd, J=13.7, 8.5 Hz, 1H), 1.88 (d, J=3.0 Hz, 1H).

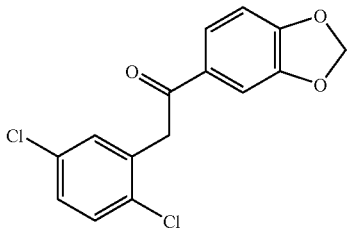

B. 1-Benzo[1,3]dioxol-5-yl-2-(2,5-dichloro-phenyl)-ethanone. To a stirred solution of the alcohol from step A (7.08 g, 22.7 mmol) in $CH_2Cl_2$ (300 mL) under $N_2$ at 0° C. was added Dess-Martin reagent (12.5 g, 29.5 mmol) in portions. The reaction mixture was allowed to warm to rt and was stirred for 2 h. The mixture was then poured into a vigorously stirred solution of $Na_2S_2O_3$ (~51 g) in satd aq $Na_2HCO_3$ (200 mL), and the resulting mixture was stirred for 1.5 h. The layers were separated, and the organic layer was washed with brine, dried ($Na_2SO_4$), and concentrated under reduced pressure. The crude ketone was carried on without further purification (6.40 g, 91%). HPLC: $R_t$=2.94 (Method A). MS (ESI): mass calculated for $C_{15}H_{10}Cl_2O_3$, 308.00. m/z found, 309.0 [M+H]$^+$. $^1$H NMR (500 MHz, $CDCl_3$): 7.65 (dd, J=8.2, 1.6 Hz, 1H), 7.49 (d, J=1.6 Hz, 1H), 7.33 (d, J=8.5 Hz, 1H), 7.25 (d, J=2.5 Hz, 1H), 7.21 (dd, J=2.7, 8.5 Hz, 1H), 6.89 (d, J=8.2 Hz, 1H), 6.07 (s, 2H), 4.32 (s, 2H), 1.55 (s, 1H).

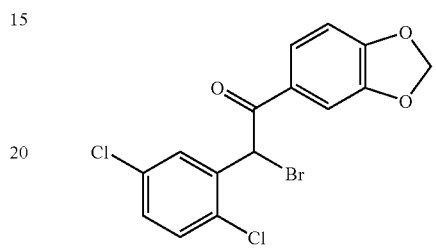

C. 1-Benzo[1,3]dioxol-5-yl-2-bromo-2-(2,5-dichloro-phenyl)-ethanone. To a stirred solution of the ketone from step B (5.30 g, 17.1 mmol) in $CH_2Cl_2$ (40 mL) under $N_2$ at 0° C. was added a solution of $Br_2$ (3.07 g, 19.2 mmol) in AcOH (100 mL) dropwise over a period of 10 min. The reaction mixture was stirred overnight, and the solvent was removed under reduced pressure. The residue was then dissolved in EtOAc (200 mL) and satd aq $NaHCO_3$ (150 mL) was added slowly. The layers were separated, and the organic layer was washed with brine, dried ($Na_2SO_4$) and concentrated under reduced pressure. The crude solid residue was carried on without further purification. HPLC: $R_t$=1.57 (Method D). $^1$H NMR (500 MHz, $CDCl_3$): 7.67 (d, J=2.5 Hz, 1H), 7.60 (dd, J=8.2, 2.0 Hz, 1H), 7.47 (d, J=1.8 Hz, 1H), 7.33 (d, J=8.6 Hz, 1H), 6.86 (d, J=8.2 Hz, 1H), 6.73 (s, 1H), 6.07 (s, 2H), 1.55 (br s, 1H).

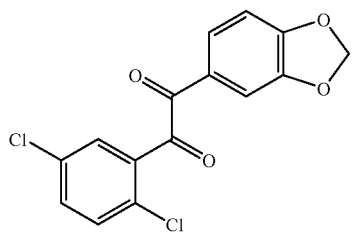

D. 1-[Benzo1,3]dioxol-5-yl-2-(2,5-dichloro-phenyl)-ethane-1,2-dione. The crude bromide from step C was dissolved in DMSO (35 mL), and the solution was heated to 65° C. for 6 h. The solution was then cooled to rt, and $Et_2O$ (200 mL) and $H_2O$ (100 mL) were added. The layers were separated, and the organic layer was washed with $H_2O$ then brine, dried ($Na_2SO_4$), and concentrated under reduced pressure. The resulting solid was vigorously stirred in $Et_2O$ (100 mL), filtered off, washed with $Et_2O$ (100 mL), and dried under vacuum. The crude, bright yellow solid was carried on without further purification (4.0 g, 72%). HPLC: $R_t$=1.47 (Method D). $^1$H NMR (500 MHz, $CDCl_3$): 7.84 (d, J=2.7 Hz, 1H), 7.61 (dd, J=8.2, 1.9

Hz, 1H), 7.51 (d, J=1.6 Hz, 1H), 7.49 (dd, J=8.5, 2.7 Hz, 1H), 7.36 (d, J=8.5 Hz, 1H), 6.93 (d, J=8.0 Hz, 1H), 6.11 (s, 2H).

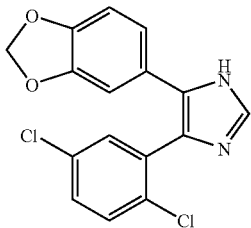

E. 5-Benzo[1,3]dioxol-5-yl-4-(2,5-dichloro-phenyl)-1H-imidazole. A suspension of the diketone from step D (3.70 g, 11.4 mmol), hexamethylenetetramine (HMTA; 4.82 g, 34.4 mmol) and NH₄OAc (5.27 g, 68.7 mmol) in AcOH (23 mL) was heated to 95° C. After 30 min, additional AcOH (17 mL) was added, and the resulting solution was stirred for 2 h. The solution was allowed to cool to rt, and solvent was removed under reduced pressure. The residue was dissolved in EtOAc (200 mL), and satd aq NaHCO₃ (150 mL) was added slowly. The resulting layers were separated, and the organic layer was washed with brine, dried (Na₂SO₄), and concentrated under reduced pressure. The resulting crude solid was carried on without further purification (3.8 g, 100%). HPLC: R$_f$=0.84 (Method D). MS (ESI): mass calculated for C$_{16}$H$_{10}$Cl$_2$N$_2$O$_2$, 332.01. m/z found, 333.0 [M+H]⁺. ¹H NMR (500 MHz, CDCl₃): 7.72 (s, 1H), 7.43-7.37 (m, 2H), 7.29-7.27 (m, 1H), 6.84 (br s, 2H), 6.76-6.74 (m, 1H), 5.96 (s, 2H).

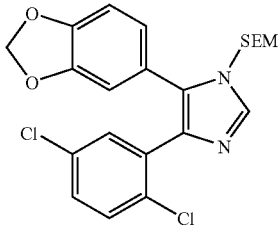

F. 5-Benzo[1,3]dioxol-5-yl-4-(2,5-dichloro-phenyl)-1-(2-trimethylsilanyl-ethoxymethyl)-1H-imidazole. To a stirred solution of the imidazole from step E (3.80 g, 11.3 mmol) in DMF (30 mL) under N₂ at 0° C. was added NaH (60% dispersion in mineral oil; 0.59 g, 14.8 mmol), and the reaction mixture was stirred for 35 min. 2-(Trimethylsilyl)ethoxymethyl chloride (SEM-Cl; 2.21 mL, 12.4 mmol) was added in one portion, and the resulting mixture was allowed to warm to rt and was stirred for 40 min. The solvent was removed under reduced pressure, and EtOAc (100 mL) and H₂O (100 mL) were added to the residue. The layers were separated, and the organic layer was washed with brine, dried (Na₂SO₄), and concentrated under reduced pressure. The crude solid residue was purified on silica gel (CH₂Cl₂) to afford an inseparable mixture of regioisomers (3.25 g, 62%). HPLC: R$_f$=1.30 (Method D). MS (ESI): mass calculated for C$_{22}$H$_{24}$Cl$_2$N$_2$O$_3$Si, 462.09. m/z found, 463.1 [M+H]⁺. ¹H NMR of mixture of two isomers (500 MHz, CDCl₃): Isomer 1: 7.77 (s, 1H), 7.52 (d, J=8.6 Hz, 1H), 7.44 (dd, J=8.6, 2.5 Hz, 1H), 7.41 (d, J=2.5 Hz, 1H), 7.00 (d, J=1.3 Hz, 1H), 6.97 (dd, J=8.0, 1.5 Hz, 1H), 6.74 (d, J=8.0 Hz, 1H), 5.96 (s, 2H), 5.18 (d, J=10.9 Hz, 1H), 5.03 (d, J=10.9 Hz, 1H), 3.42 (t, J=8.1 Hz, 2H), 0.89-0.85 (m, 2H), 0.00 (s, 9H); Isomer 2: 7.78 (s, 1H), 7.45 (d, J=2.5 Hz, 2H), 7.43 (d, J=2.5 Hz, 1H), 7.42 (d, J=2.5 Hz, 1H) 7.31 (d, J=8.6 Hz, 1H), 7.22 (dd, J=8.6, 2.5 Hz, 1H), 6.84 (d, J=1.6 Hz, 1H) 6.02 (s, 2H), 5.26 (s, 2H), 3.62-3.57 (m, 1H), 0.99-0.95 (m, 2H), 0.05 (s, 9H).

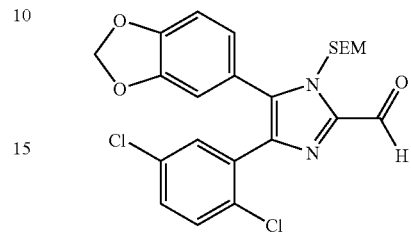

G. 5-Benzo[1,3]dioxol-5-yl-4-(2,5-dichloro-Phenyl)-1-(2-trimethylsilanyl-ethoxymethyl)-1H-imidazole-2-carbaldehyde. To a stirred solution of the imidazole from step F (3.25 g, 7.01 mmol) in THF (30 mL) under N₂ at −78° C. was added lithium diisopropylamide (2.0 M LDA in THF; 4.21 mL, 8.41 mmol), and the reaction mixture was stirred for 35 min. To this mixture was added dry DMF (2.71 mL, 35.1 mmol) in one portion, and the resulting mixture was allowed to warm to rt and was stirred for 2 h. Twenty milliliters of 1 N HCl was added. The reaction mixture was stirred for 1 h, and then EtOAc (100 mL) and H₂O (100 mL) were added. The layers were separated, and the organic layer was washed with brine, dried (Na₂SO₄), and concentrated under reduced pressure. The crude solid residue was purified on silica gel (EtOAc/hexanes) to afford an inseparable mixture of regioisomers (2.11 g, 62%). MS (ESI): mass calculated for C$_{23}$H$_{24}$Cl$_2$N$_2$O$_4$Si, 490.09. m/z found, 491.0 [M+H]⁺. ¹H NMR of mixture of two isomers (400 MHz, CDCl₃): Isomer 1: 9.98 (s, 1H), 7.04 (dd, J=1.8, 0.4 Hz, 2H), 6.98 (dd, J=8.0, 1.8 Hz, 2H), 6.78 (d, J=8.0 Hz, 2H), 6.00 (s, 2H), 5.89 (d, J=10.2 Hz, 1H), 5.74 (s, 1H), 5.38 (d, J=10.4 Hz, 1H), 3.76-3.72 (m, 1H), 1.03-0.98 (m, 2H), 0.00 (s, 9H); Isomer 2: 9.94 (s, 1H), 7.55 (dd, J=8.6, 0.6 Hz, 2H), 7.51 (dd, J=8.6, 2.3 Hz, 2H), 7.47 (dd, J=2.3, 0.6 Hz, 2H), 6.06 (s, 2H), 5.89 (d, J=10.2 Hz, 1H), 5.74 (s, 1H), 5.38 (d, J=10.4 Hz, 1H), 3.57-3.47 (m, 1H), 0.92-0.84 (m, 2H), 0.00 (s, 9H).

H. (Z)-3-[5-Benzo[1.3]dioxol-5-yl-4-(2,5-dichloro-Phenyl)-1H-imidazol-2-yl]-2-(3-chloro-phenyl)-acrylic acid. To a stirred solution of the aldehyde from Step G (0.10 g, 0.20 mmol) and (3-chloro-phenyl)-acetic acid (52 mg, 0.31 mmol) in Ac₂O (0.3 mL) was added Et₃N (0.3 mL). The mixture was stirred for 30 min, and the solution volume was decreased under reduced pressure. The crude mixture was filtered through silica (0-10% MeOH/CH₂Cl₂), and the filtrate was concentrated to afford crude SEM-protected imidazole (119 mg). Trifluoroacetic acid (TFA; 0.5 mL) was added to a solution of the residue in CH₂Cl₂ (0.5 mL), and the mixture was stirred at rt for ~6 h. The solvent was removed under reduced pressure, and the residue was purified by reversed-phase chromatography (Method B) to provide the E-stereoisomer (Example 2) and the title Z-stereoisomer (42 mg, 40%). HPLC: R$_f$=1.39 (Method D). MS (ESI): mass calculated for C$_{25}$H$_{15}$Cl$_3$N$_2$O$_4$, 512.01. m/z found, 513.2 [M+H]⁺. ¹H NMR (400 MHz, CDCl₃): 7.36 (t, J=2.0 Hz, 1H), 7.35-7.31 (m, 2H), 7.29-7.25 (m, 2H), 7.22 (td, J=7.6, 1.3 Hz, 1H), 7.11-7.07

(m, 1H), 6.95 (s, 1H), 6.79 (dd, J=8.1, 1.8 Hz, 1H), 6.72 (d, J=1.8 Hz, 1H), 6.67 (d, J=8.1 Hz, 1H), 5.90 (s, 2H).

Example 2

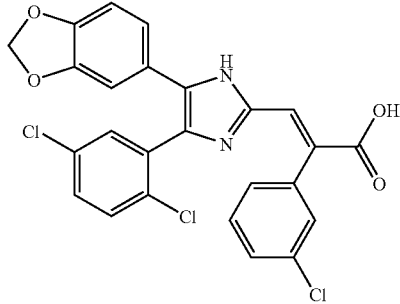

(E)-3-[5-Benzo[1,3]dioxol-5-yl-4-(2,5-dichloro-phenyl)-1H-imidazol-2-yl]-2-(3-chloro-phenyl)-acrylic acid.

The title compound was prepared as described in Example 1 and isolated by reversed-phase chromatography (Method B) to afford 42 mg (40%) of the desired acid. HPLC: $R_t$=1.22 (Method D). MS (ESI): mass calculated for $C_{25}H_{15}Cl_3N_2O_4$, 512.01. m/z found, 513.2 [M+H]$^+$. $^1$H NMR (500 MHz, CDCl$_3$): 8.06 (s, 1H), 7.47 (t, J=7.4 Hz, 1H), 7.39-7.33 (m, 2H), 7.32-7.20 (m, 4H), 6.72 (d, J=8.2 Hz, 1H), 6.57 (br d, J=7.7 Hz, 1H), 6.51 (br s, 1H), 5.97 (s, 2H).

Example 3

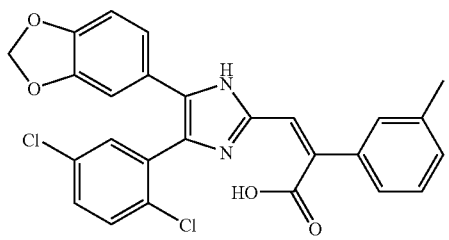

(Z)-3-[5-Benzo[1,3]dioxol-5-yl-4-(2,5-dichloro-phenyl)-1H-imidazol-2-yl]-2-m-tolyl-acrylic acid.

The title compound was prepared as in Example 1 and Scheme A, substituting m-tolyl-acetic acid for (3-chloro-phenyl)-acetic acid in step H (5% yield). HPLC: $R_t$=1.28 (Method D). MS (ESI): mass calculated for $C_{26}H_{18}Cl_2N_2O_4$, 492.06. m/z found, 493.2 [M+H]$^+$. $^1$H NMR (500 MHz, CDCl$_3$): 7.47-7.40 (m, 2H), 7.19 (br s, 1H), 7.15 (br d, J=8.0 Hz, 1H), 7.01-6.96 (m, 3H), 6.92 (br d, J=7.7 Hz, 1H), 6.84 (d, J=8.0 Hz, 1H), 6.70 (dd, J=8.2, 1.9 Hz, 1H), 6.52 (d, J=1.6 Hz, 1H), 6.05 (s, 2H), 2.12 (s, 3H).

Example 4

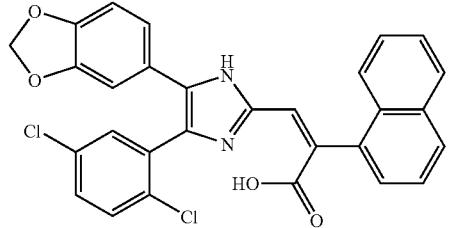

(Z)-3-[5-Benzo[1,3]dioxol-5-yl-4-(2,5-dichloro-phenyl)-1H-imidazol-2-yl]-2-naphthalen-1-yl-acrylic acid.

The title compound was prepared as in Example 1 and Scheme A, substituting naphthalen-1-yl-acetic acid for (3-chloro-phenyl)-acetic acid in step H (3% yield). HPLC: $R_t$=1.40 (Method D). MS (ESI): mass calculated for $C_{29}H_{18}Cl_2N_2O_4$, 528.06. m/z found, 529.2 [M+H]$^+$. $^1$H NMR (500 MHz, CDCl$_3$): 7.78 (br d, J=8.8 Hz, 1H), 7.74 (br d, J=8.0 Hz, 1H), 7.64-7.61 (m, 1H), 7.53-7.46 (m, 2H), 7.43-7.39 (m, 3H), 7.09 (s, 1H), 6.86 (br s, 1H), 6.80 (br d, J=7.7 Hz, 1H), 6.67 (br d, J=9.0 Hz, 1H), 6.49 (s, 1H), 6.05 (s5 2H).

Example 5

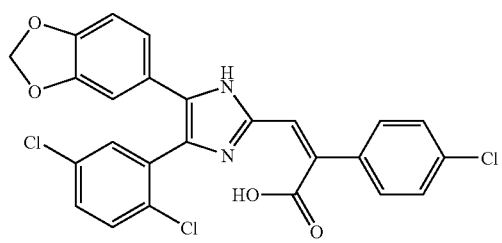

(Z)-3-[5-Benzo[1,3]dioxol-5-yl-4-(2,5-dichloro-phenyl)-1H-imidazol-2-yl]-2-(4-chloro-phenyl)-acrylic acid.

The title compound was prepared as in Example 1 and Scheme A, substituting (4-chloro-phenyl)-acetic acid for (3-chloro-phenyl)-acetic acid in step H (6% yield). HPLC: $R_t$=1.39 (Method D). MS (ESI): mass calculated for $C_{25}H_{15}Cl_3N_2O_4$, 512.01. m/z found, 513.2 [M+H]$^+$. $^1$H NMR (500 MHz, CDCl$_3$): 7.45-7.41 (m, 2H), 7.29 (br d, J=8.5 Hz, 2H), 7.20 (s, 1H), 7.08 (br d, J=8.5 Hz, 2H), 6.98 (s, 1H), 6.83 (br d, J=8.2 Hz, 1H), 6.78-6.75 (m, 1H), 6.62 (br s, 1H), 6.03 (s, 2H).

Example 6

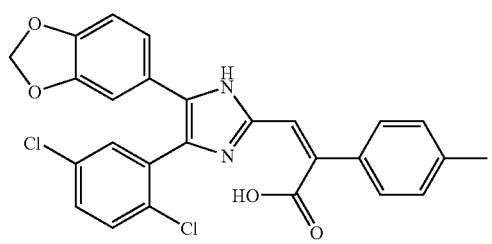

(Z)-3-[5-Benzo[1,3]dioxol-5-yl-4-(2,5-dichloro-phenyl)-1H-imidazol-2-yl]-2-p-tolyl-acrylic acid.

The title compound was prepared as in Example 1 and Scheme A, substituting p-tolyl-acetic acid for (3-chloro-phenyl)-acetic acid in step H (6% yield). HPLC: $R_f$=1.26 (Method D). MS (ESI): mass calculated for $C_{26}H_{18}Cl_2N_2O_4$, 492.06; m/z found, 493.2 [M+H]$^+$. $^1$H NMR (500 MHz, CDCl$_3$): 7.44 (d, J=8.5 Hz, 1H), 7.39 (dd, J=8.5, 2.2 Hz, 1H), 7.27-7.23 (m, 2H), 7.17 (br d, J=1.9 Hz, 1H), 6.97-6.92 (m, 3H), 6.83-6.77 (m, 2H), 6.64 (s, 1H), 6.01 (s, 2H), 2.18 (s, 3H).

Example 7

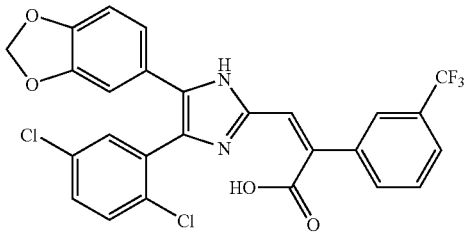

(Z)-3-[5-Benzo[1,3]dioxol-5-yl-4-(2,5-dichloro-phenyl)-1H-imidazol-2-yl]-2-(3-trifluoromethyl-phenyl)-acrylic acid.

The title compound was prepared as in Example 1 and Scheme A, substituting (3-trifluoromethyl-phenyl)-acetic acid for (3-chloro-phenyl)-acetic acid in step H (6% yield). HPLC: $R_f$=1.44 (Method D). MS (ESI): mass calculated for $C_{26}H_{15}Cl_2F_3N_2O_4$, 546.04. m/z found, 547.2 [M+H]$^+$. $^1$H NMR (500 MHz, CDCl$_3$): 7.67 (s, 1H), 7.57 (br d, J=9.0 Hz, 1H), 7.47-7.36 (m, 3H), 7.27-7.22 (m, 1H), 7.13-7.07 (m, 2H), 6.81 (d, J=8.0 Hz, 1H), 6.71 (dd, J=8.2, 1.9 Hz, 1H), 6.59 (d, J=1.6 Hz, 1H), 6.03 (s, 2H).

Example 8

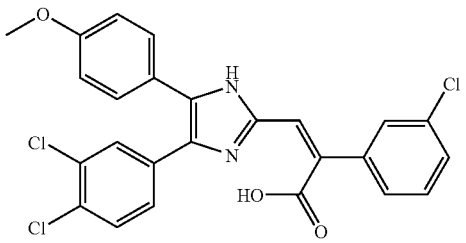

(Z)-2-(3-Chloro-phenyl)-3-[4-(3,4-dichloro-phenyl)-5-(4-methoxy-phenyl)-1H-imidazol-2-yl]-acrylic acid.

The title compound was prepared as in Example 1 and Scheme A, substituting (3,4-dichloro-benzyl)-magnesium bromide for (2,5-dichloro-benzyl)-magnesium bromide, and 4-methoxy-benzaldehyde for benzo[1,3]dioxole-5-carbaldehyde in step A (4% overall yield). HPLC: $R_f$=1.51 (Method D). MS (ESI): mass calculated for $C_{25}H_{17}Cl_3N_2O_3$, 498.03. m/z found, 499.0 [M+H]$^+$. $^1$H NMR (400 MHz, CDCl$_3$): 7.48-7.44 (m, 2H), 7.37 (br s, 1H), 7.30-7.20 (m, 3H), 7.06-6.99 (m, 3H), 6.94 (d, J=8.5 Hz, 2H), 3.86 (s, 3H).

Example 9

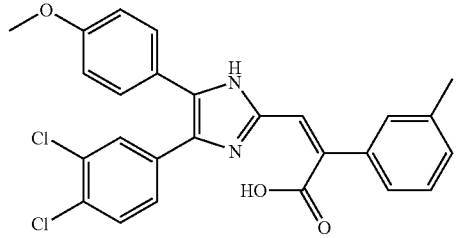

(Z)-3-[4-(3,4-Dichloro-phenyl)-5-(4-methoxy-phenyl)-1H-imidazol-2-yl]-2-m-tolyl-acrylic acid.

The title compound was prepared as in Example 1 and Scheme A, substituting (3,4-dichloro-benzyl)-magnesium bromide for (2,5-dichloro-benzyl)-magnesium bromide, and 4-methoxy-benzaldehyde for benzo[1,3]dioxole-5-carbaldehyde in step A, and substituting m-tolyl-acetic acid for (3-chloro-phenyl)-acetic acid in step H (3% overall yield). HPLC: $R_f$=1.38 (Method D). MS (ESI): mass calculated for $C_{26}H_{20}Cl_2N_2O_3$, 478.09. m/z found, 479.1 [M+H]$^+$. $^1$H NMR (400 MHz, CDCl$_3$): 7.46 (br d, J=8.3 Hz, 1H), 7.37 (br s, 1H), 7.27-7.23 (m, 2H), 7.21-7.16 (m, 2H), 7.12 (br d, J=6.8 Hz, 1H), 6.98-6.88 (m, 5H), 3.87 (s, 3H), 2.08 (s, 3H).

Example 10

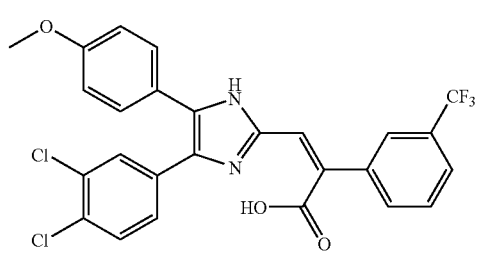

(Z)-3-[4-(3,4-Dichloro-phenyl)-5-(4-methoxy-phenyl)-1H-imidazol-2-yl]-2-(3-trifluoromethyl-phenyl)-acrylic acid.

The title compound was prepared as in Example 1 and Scheme A, substituting (3,4-dichloro-benzyl)-magnesium bromide for (2,5-dichloro-benzyl)-magnesium bromide, and 4-methoxy-benzaldehyde for benzo[1,3]dioxole-5-carbaldehyde in step A, and substituting (3-trifluoromethyl-phenyl)-acetic acid for (3-chloro-phenyl)-acetic acid in step H (7% overall yield). HPLC: $R_f$=1.58 (Method D). MS (ESI): mass calculated for $C_{26}H_{17}Cl_2F_3N_2O_3$, 532.06. m/z found, 533.1 [M+H]$^+$. $^1$H NMR (400 MHz, CDCl$_3$): 7.67 (br s, 1H), 7.55 (br d, J=8.1 Hz, 1H), 7.45 (d, J=2.0 Hz, 1H), 7.39 (br d, J=7.6 Hz, 1H), 7.35 (d, J=8.3 Hz, 1H), 7.26-7.20 (m, 3H), 7.18 (dd, J=8.3, 2.0 Hz, 1H), 7.09 (s, 1H), 6.85 (d, J=8.8 Hz, 2H), 3.79 (s, 3H).

Example 11

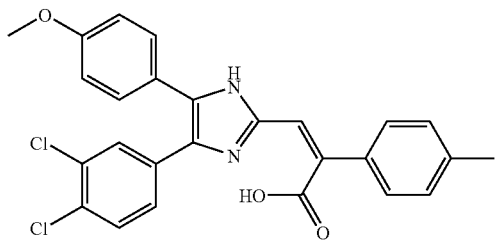

(Z)-3-[4-(3,4-Dichloro-phenyl)-5-(4-methoxy-phenyl)-1H-imidazol-2-yl]-2-p-tolyl-acrylic acid.

The title compound was prepared as in Example 1 and Scheme A, substituting (3,4-dichloro-benzyl)-magnesium bromide for (2,5-dichloro-benzyl)-magnesium bromide, and 4-methoxy-benzaldehyde for benzo[1,3]dioxole-5-carbaldehyde in step A, and substituting p-tolyl-acetic acid for (3-chloro-phenyl)-acetic acid in step H (7% overall yield). HPLC: $R_t$=1.28 (Method D). MS (ESI): mass calculated for $C_{26}H_{20}Cl_2N_2O_3$, 478.09. m/z found, 479.1 $[M+H]^+$. $^1H$ NMR (400 MHz, $CDCl_3$): 7.90 (s, 1H), 7.37 (d, J=8.3 Hz, 1H), 7.29 (d, J=2.0 Hz, 1H), 7.28-7.24 (m, 2H), 7.21 (d, J=8.0 Hz, 2H), 7.12 (dd, J=8.3, 2.0 Hz, 1H), 7.10 (d, J=8.8 Hz, 2H), 6.84 (d, J=8.8 Hz, 2H), 3.81 (s, 3H), 2.40 (s, 3H).

Example 12

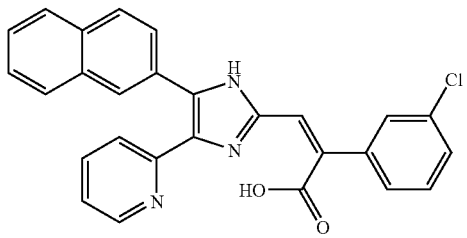

(Z)-2-(3-Chloro-phenyl)-3-(5-naphthalen-2-yl-4-pyridin-2-yl-1H-imidazol-2-yl)-acrylic acid.

The title compound was prepared as described in Schemes A and B, starting with the coupling of 2-ethynyl-naphthalene and 2-iodo-pyridine (Scheme B) to prepare the diketone intermediate A5 of Scheme A.

Example 13

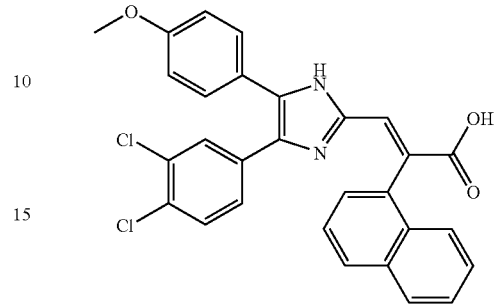

(E)-3-[4-(3,4-Dichloro-phenyl)-5-(4-methoxy-phenyl)-1H-imidazol-2-yl]-2-naphthalen-1-yl-acrylic acid.

The title compound was prepared as in Examples 1 and 2 and Scheme A, substituting (3,4-dichloro-benzyl)-magnesium bromide for (2,5-dichloro-benzyl)-magnesium bromide, and 4-methoxy-benzaldehyde for benzo[1,3]dioxole-5-carbaldehyde in step A of Example 1, and substituting naphthalen-1-yl-acetic acid for (3-chloro-phenyl)-acetic acid in step H of Example 1 (7% overall yield). HPLC: $R_t$=1.46 (Method D). MS (ESI): mass calculated for $C_{29}H_{20}Cl_2N_2O_3$, 514.09. m/z found, 515.1 $[M+H]^+$. $^1H$ NMR (400 MHz, $CDCl_3$): 8.34 (s, 1H), 8.07 (d, J=8.0 Hz, 1H), 8.00 (d, J=8.0 Hz, 1H), 7.85 (d, J=8.0 Hz, 1H), 7.68-7.51 (m, 4H), 7.31 (d, J=8.3 Hz, 1H), 7.24 (d, J=2.0 Hz, 1H), 7.06 (dd, J=8.6, 2.0 Hz, 1H), 6.76 (d, J=2.0 Hz, 4H), 3.78 (s, 3H).

Example 14

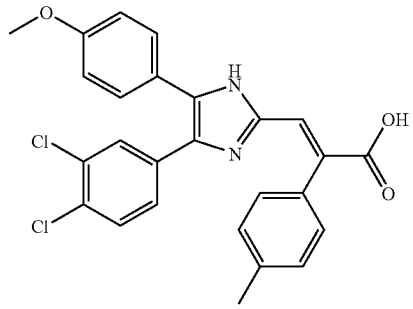

(E)-3-[4-(3,4-Dichloro-phenyl)-5-(4-methoxy-phenyl)-1H-imidazol-2-yl]-2-p-tolyl-acrylic acid.

The title compound was prepared as in Examples 1 and 2 and Scheme A, substituting (3,4-dichloro-benzyl)-magnesium bromide for (2,5-dichloro-benzyl)-magnesium bromide, and 4-methoxy-benzaldehyde for benzo[1,3]dioxole-5-carbaldehyde in step A of Example 1, and substituting p-tolyl-acetic acid for (3-chloro-phenyl)-acetic acid in step H of Example 1 (10% overall yield). HPLC: $R_t$=1.28 (Method D). MS (ESI): mass calculated for $C_{26}H_{20}Cl_2N_2O_3$, 478.09; m/z found, 479.1 [M+H]$^+$. $^1$H NMR (400 MHz, CDCl$_3$): 7.90 (s, 1H), 7.37 (d, J=8.4 Hz, 1H), 7.29 (d, J=2.0 Hz, 1H), 7.26 (d, J=8.0 Hz, 2H), 7.20 (d, J=8.0 Hz, 2H), 7.12 (dd, J=8.4, 2.0 Hz, 1H), 7.09 (d, J=8.8 Hz, 2H), 6.84 (d, J=8.8 Hz, 2H), 3.81 (s, 3H), 2.40 (s, 3H).

Example 15

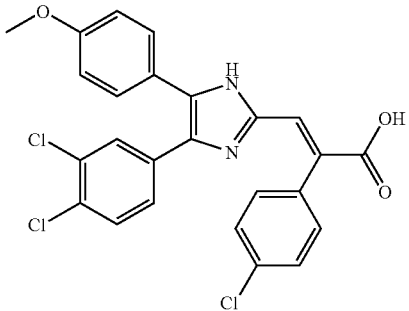

(E)-2-(4-Chloro-phenyl)-3-[4-(3,4-dichloro-phenyl)-5-(4-methoxy-phenyl)-1H-imidazol-2-yl]-acrylic acid.

The title compound was prepared as in Examples 1 and 2 and Scheme A, substituting (3,4-dichloro-benzyl)-magnesium bromide for (2,5-dichloro-benzyl)-magnesium bromide, and 4-methoxy-benzaldehyde for benzo[1,3]dioxole-5-carbaldehyde in step A of Example 1, and substituting (4-chloro-phenyl)-acetic acid for (3-chloro-phenyl)-acetic acid in step H of Example 1 (11% overall yield). HPLC: $R_t$=1.35 (Method D). MS (ESI): mass calculated for $C_{25}H_{17}Cl_3N_2O_3$, 498.0. m/z found, 499.0 [M+H]$^+$. $^1$H NMR (400 MHz, CDCl$_3$): 7.94 (s, 1H), 7.40 (d, J=8.6 Hz, 2H), 7.37 (d, J=2.0 Hz, 1H), 7.35 (d, J=8.3 Hz, 1H), 7.28-7.24 (m, 2H), 7.13 (dd, J=8.3, 2.0 Hz, 1H), 7.07 (d, J=8.8 Hz, 2H), 6.85 (d, J=8.8 Hz, 2H), 3.82 (s, 3H).

Example 16

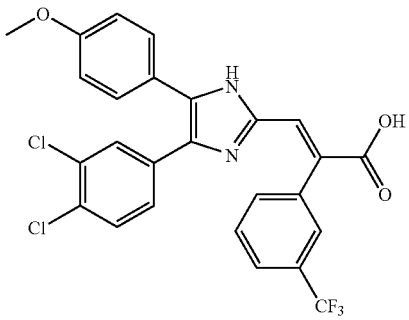

(E)-3-[4-(3,4-Dichloro-phenyl)-5-(4-methoxy-phenyl)-1H-imidazol-2-yl]-2-(3-trifluoromethyl-phenyl)-acrylic acid.

The title compound was prepared as in Examples 1 and 2 and Scheme A, substituting (3,4-dichloro-benzyl)-magnesium bromide for (2,5-dichloro-benzyl)-magnesium bromide, and 4-methoxy-benzaldehyde for benzo[1,3]dioxole-5-carbaldehyde in step A of Example 1, and substituting (3-trifluoromethyl-phenyl)-acetic acid for (3-chloro-phenyl)-acetic acid in step H of Example 1 (10% overall yield). HPLC: $R_t$=1.46 (Method D). MS (ESI): mass calculated for $C_{26}H_{17}Cl_2F_3N_2O_3$, 532.06. m/z found, 533.1 [M+H]$^+$. $^1$H NMR (400 MHz, CDCl$_3$): 7.99 (s, 1H), 7.63 (br d, J=7.8 Hz, 1H), 7.50-7.40 (m, 3H), 7.23-7.25 (m, 2H), 7.07-7.00 (m, 3H), 6.78 (d, J=8.8 Hz, 2H), 3.78 (s, 3H).

Example 17

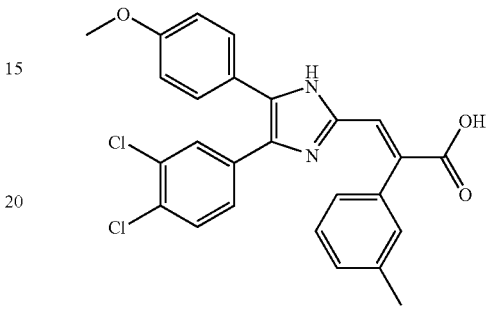

(E)-3-[4-(3,4-Dichloro-phenyl)-5-(4-methoxy-phenyl)-1H-imidazol-2-yl]-2-m-tolyl-acrylic acid.

The title compound was prepared as in Examples 1 and 2 and Scheme A, substituting (3,4-dichloro-benzyl)-magnesium bromide for (2,5-dichloro-benzyl)-magnesium bromide, and 4-methoxy-benzaldehyde for benzo[1,3]dioxole-5-carbaldehyde in step A of Example 1, and substituting imtolyl-acetic acid for (3-chloro-phenyl)-acetic acid in step H of Example 1 (3% yield). HPLC: $R_t$=1.30 (Method D). MS (ESI): mass calculated for $C_{26}H_{20}Cl_2N_2O_3$, 478.09. m/z found, 479.1 [M+H]$^+$. $^1$H NMR (400 MHz, CDCl$_3$): 8.03 (s, 1H), 7.49-7.43 (m, 1H), 7.40-7.35 (m, 3H), 7.23-7.15 (m, 3H), 7.06 (d, J=8.8 Hz, 2H), 6.85 (d, J=8.8 Hz, 2H), 3.82 (s, 3H), 2.41 (s, 2H).

Example 18

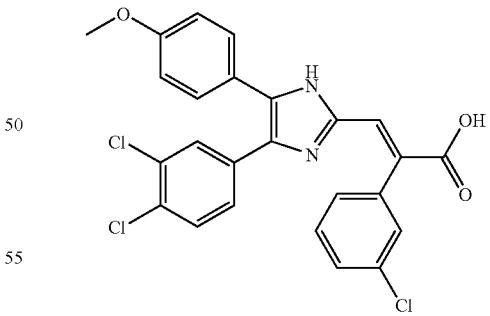

(E)-2-(3-Chloro-phenyl)-3-[4-(3,4-dichloro-phenyl)-5-(4-methoxy-phenyl)-1H-imidazol-2-yl]-acrylic acid.

The title compound was prepared as in Examples 1 and 2 and Scheme A, substituting (3,4-dichloro-benzyl)-magnesium bromide for (2,5-dichloro-benzyl)-magnesium bromide, and 4-methoxy-benzaldehyde for benzo[1,3]dioxole-5-carbaldehyde in step A of Example 1 (4% overall yield). HPLC: $R_t$=1.43 (Method D). MS (ESI): mass calculated for $C_{25}H_{17}Cl_3N_2O_3$, 498.03. m/z found, 499.0 [M+H]$^+$. $^1$H NMR (400 MHz, CDCl$_3$): 8.10 (s, 1H), 7.44 (br d, J=7.8 Hz, 1H), 7.40-7.33 (m, 4H), 7.23 (br d, J=7.6 Hz, 1H), 7.15 (dd, J=8.3, 2.0 Hz, 1H), 7.10 (d, J=8.8 Hz, 2H), 6.85 (d, J=8.8 Hz, 2H), 3.81 (s, 3H).

Example 19

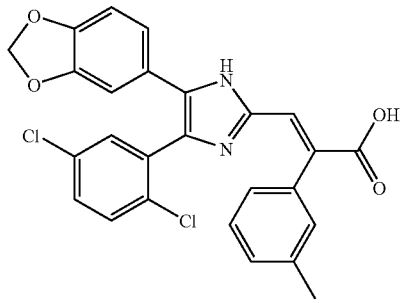

(E)-3-[5-Benzo[1,3]dioxol-5-yl-4-(2,5-dichloro-phenyl)-1H-imidazol-2-yl]-2-m-tolyl-acrylic acid.

The title compound was prepared as in Examples 1 and 2 and Scheme A, substituting m-tolyl-acetic acid for (3-chloro-phenyl)-acetic acid in step H of Example 1 (6% overall yield). HPLC: R$_f$=1.16 (Method D). MS (ESI): mass calculated for $C_{26}H_{18}Cl_2N_2O_4$, 492.06. m/z found, 493.2 [M+H]$^+$. $^1$H NMR (500 MHz, CDCl$_3$): 8.06 (s, 1H), 7.49-7.44 (m, 1H), 7.38-7.20 (m, 5H), 6.72 (d, J=8.2 Hz, 1H), 6.57 (br d, J=8.0 Hz, 1H), 6.51 (br s, 1H), 5.97 (s, 3H), 2.42 (s, 3H).

Example 20

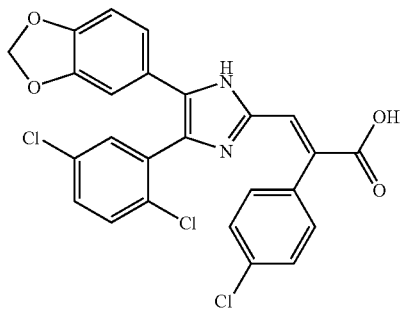

(E)-3-[5-Benzo[1,3]dioxol-5-yl-4-(2,5-dichloro-phenyl)-1H-imidazol-2-yl]-2-(4-chloro-phenyl)-acrylic acid.

The title compound was prepared as in Examples 1 and 2 and Scheme A, substituting (4-chloro-phenyl)-acetic acid for (3-chloro-phenyl)-acetic acid in step H of Example 1 (10% overall yield). HPLC: R$_f$=1.21 (Method D). MS (ESI): mass calculated for $C_{25}H_{15}Cl_3N_2O_4$, 512.01. m/z found, 513.2 [M+H]$^+$. $^1$H NMR (500 MHz, CDCl$_3$): 8.00 (s, 1H), 7.40 (d, J=8.5 Hz, 2H), 7.37 (d, J=8.5 Hz, 1H), 7.32 (dd, J=8.5, 2.2 Hz, 1H), 7.29-7.25 (m, 2H), 7.22 (d, J=2.5 Hz, 1H), 6.74 (d, J=8.2 Hz, 1H), 6.66 (dd, J=8.0, 1.6 Hz, 1H), 6.58 (d, J=2.0 Hz, 1H), 5.97 (s, 2H).

Example 21

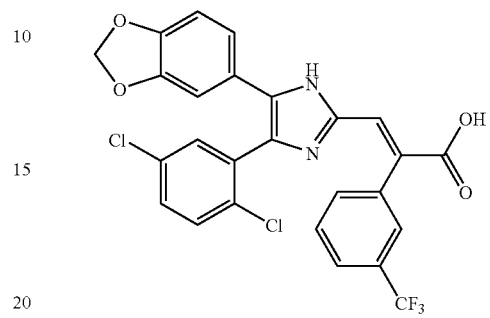

(E)-3-[5-Benzo[1,3]dioxol-5-yl-4-(2,5-dichloro-phenyl)-1H-imidazol-2-yl]-2-(3-trifluoromethyl-phenyl)-acrylic acid.

The title compound was prepared as in Examples 1 and 2 and Scheme A, substituting (3-trifluoromethyl-phenyl)-acetic acid for (3-chloro-phenyl)-acetic acid in step H of Example 1 (11% overall yield). HPLC: R$_f$=1.30 (Method D). MS (ESI): mass calculated for $C_{26}H_{15}Cl_2F_3N_2O_4$, 546.04. m/z found, 547.2 [M+H]$^+$. $^1$H NMR (500 MHz, CDCl$_3$): 8.09 (s, 1H), 7.71 (br d, J=5.3 Hz, 1H), 7.60 (s, 1H), 7.56 (d, J=5.2 Hz, 2H), 7.33 (d, J=8.5 Hz, 1H), 7.30 (dd, J=8.5, 2.2 Hz, 1H), 7.22 (d, J=2.2 Hz, 1H), 6.71 (d, J=8.2 Hz, 1H), 6.64 (dd, J=8.0, 1.6 Hz, 1H), 6.57 (d, J=1.6 Hz, 1H), 5.95 (s, 2H).

Example 22

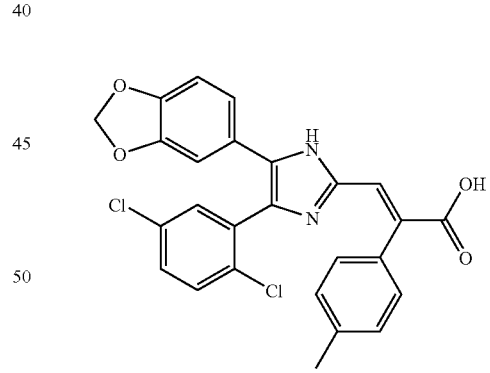

(E)-3-[5-Benzo[1,3]dioxol-5-yl-4-(2,5-dichloro-phenyl)-1H-imidazol-2-yl]-2-p-tolyl-acrylic acid.

The title compound was prepared as in Examples 1 and 2 and Scheme A, substituting ptolyl-acetic acid for (3-chloro-phenyl)-acetic acid in step H of Example 1 (10% overall yield). HPLC: R$_f$=1.16 (Method D). MS (ESI): mass calculated for $C_{26}H_{18}Cl_2N_2O_4$, 492.06. m/z found, 493.2 [M+H]$^+$. $^1$H NMR (500 MHz, CDCl$_3$): 8.02 (s, 1H), 7.38-7.34 (m, 3H), 7.31 (dd, J=8.5, 2.2 Hz, 1H), 7.30-7.23 (m, 3H), 6.72 (d, J=8.0 Hz, 1H), 6.58 (dd, J=8.2, 1.9 Hz, 1H), 6.49 (d, J=1.6 Hz, 1H), 5.97 (s, 2H), 2.44 (s, 3H).

Example 23

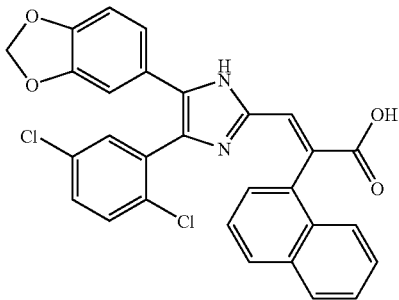

(E)-3-[5-Benzo[1,3]dioxol-5-yl-4-(2,5-dichloro-phenyl)-1H-imidazol-2-yl]-2-naphthalen-1-yl-acrylic acid.

The title compound was prepared as in Examples 1 and 2 and Scheme A, substituting naphthalen-1-yl-acetic acid for (3-chloro-phenyl)-acetic acid in step H of Example 1 (16% yield). HPLC: $R_f$=1.27 (Method D). MS (ESI): mass calculated for $C_{29}H_{18}Cl_2N_2O_4$, 528.06. m/z found, 529.2 [M+H]$^+$. $^1$H NMR (500 MHz, CDCl$_3$): 8.34 (s, 1H), 8.05 (d, J=8.2 Hz, 1H), 7.98 (d, J=8.2 Hz, 1H), 7.85 (d, J=8.2 Hz, 1H), 7.66-7.62 (m, 1H), 7.61-7.52 (m, 3H), 7.25-7.21 (m, 2H), 7.09 (d, J=2.2 Hz, 1H), 6.65 (d, J=8.0 Hz, 1H), 6.39 (br d, J=8.0 Hz, 1H), 6.35 (br s, 1H), 5.93 (s, 2H).

Example 24

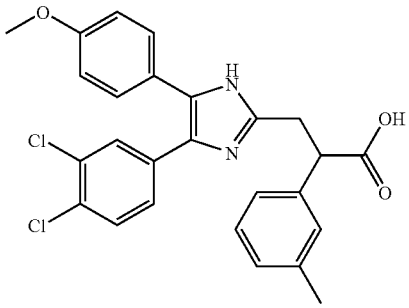

3-[4-(3,4-Dichloro-phenyl)-5-(4-methoxy-phenyl)-1H-imidazol-2-yl]-2-m-tolyl-propionic acid.

A stirred solution of (E)-3-[4-(3,4-dichloro-phenyl)-5-(4-methoxy-phenyl)-1H-imidazol-2-yl]-2-m-tolyl-acrylic acid (Example 17; 50 mg, 0.084 mmol), p-toluenesulfonylhydrazide (0.24 g, 1.26 mmol) and NaOAc (0.10 g, 1.26 mmol) in EtOH (1.0 mL) was heated to 85° C. for 16 h. The reaction mixture was cooled and then purified directly by reversed-chromatography (Method B) to afford the title compound (10 mg, 20%). HPLC: $R_f$=1.19 (Method D). MS (ESI): mass calculated for $C_{26}H_{22}Cl_2N_2O_3$, 480.10. m/z found, 481.0 [M+H]$^+$. $^1$H NMR (400 MHz, CDCl$_3$): 7.54 (d, J=2.0 Hz, 1H), 7.44 (d, J=8.3 Hz, 1H), 7.34-7.29 (m, 2H), 7.27 (dd, J=8.3, 2.0 Hz, 1H), 7.23 (d, J=7.6 Hz, 1H), 7.17-7.10 (m, 3H), 6.96-6.91 (m, 2H), 4.40 (dd, J=10.1, 5.8 Hz, 1H), 3.86 (s, 3H), 3.61 (dd, J=14.9, 10.1 Hz, 1H), 3.29 (dd, J=14.9, 5.8 Hz, 1H), 2.34 (s, 3H).

Example 25

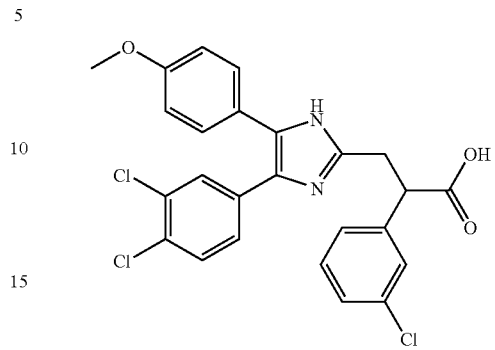

2-(3-Chloro-phenyl)-3-[4-(3,4-dichloro-phenyl)-5-(4-methoxy-phenyl)-1H-imidazol-2-yl]-propionic acid.

The title compound was prepared using the methods described in Example 24 and Scheme A substituting the olefin of Example 18 for the olefin of Example 17 (22% yield). HPLC: $R_f$=1.19 (Method D). MS (ESI): mass calculated for $C_{25}H_{19}Cl_3N_2O_3$, 500.05. m/z found, 500.1 [M+H]$^+$. $^1$H NMR (400 MHz, CDCl$_3$): 7.55 (d, J=2.0 Hz, 1H), 7.43 (d, J=8.3 Hz, 1H), 7.37-7.35 (m, 1H), 7.31-7.28 (m, 5H), 7.27 (dd, J=8.3, 2.3 Hz, 1H), 6.96-6.92 (m, 1H), 4.41 (dd, J=9.8, 6.0 Hz, 2H), 3.85 (s, 3H), 3.61 (dd, J=14.9, 9.8 Hz, 1H), 3.30 (dd, J=14.9, 6.1 Hz, 1H).

Example 26

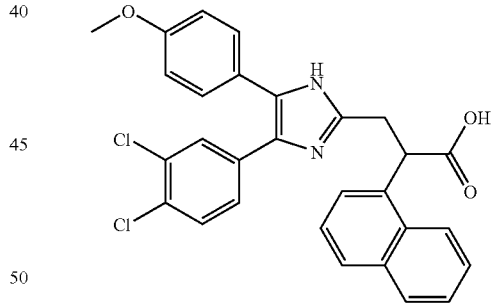

3-[4-(3,4-Dichloro-phenyl)-5-(4-methoxy-phenyl)-1H-imidazol-2-yl]-2-naphthalen-1-yl-propionic acid.

The title compound was prepared using the methods described in Example 24 and Scheme A substituting the olefin of Example 13 for the olefin of Example 17 (17% yield). HPLC: $R_f$=1.21 (Method D). MS (ESI): mass calculated for $C_{29}H_{22}Cl_2N_2O_3$, 516.10. m/z found, 517.6 [M+H]$^+$. $^1$H NMR (400 MHz, CDCl$_3$): 8.22 (d, J=8.5 Hz, 1H), 7.87 (dd, J=8.1, 1.3 Hz, 1H), 7.82 (d, J=8.1 Hz, 1H), 7.57-7.46 (m, 4H), 7.45-7.44 (m, 1H), 7.39 (d, J=8.3 Hz, 1H), 7.25-7.21 (m, 2H), 7.18 (dd, J=8.6, 2.3 Hz, 1H), 6.93-6.89 (m, 2H), 5.23 (dd, J=9.6, 6.3 Hz, 1H), 3.85 (s, 3H), 3.74 (dd, J=15.2, 9.6 Hz, 1H), 3.40 (dd, J=14.7, 6.3 Hz, 1H).

Example 27

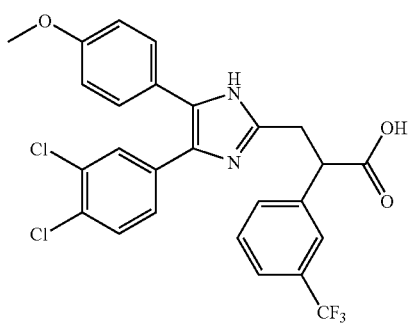

3-[4-(3,4-Dichloro-phenyl)-5-(4-methoxy-phenyl)-1H-imidazol-2-yl]-2-(3-trifluoromethyl-phenyl)-propionic acid.

The title compound was prepared using the methods described in Example 24 and Scheme A substituting the olefin of Example 16 for the olefin of Example 17 (22% yield). HPLC: $R_f$=1.18 (Method D). MS (ESI): mass calculated for $C_{26}H_{19}Cl_2F_3N_2O_3$, 534.07. m/z found, 535.0 [M+H]$^+$. $^1$H NMR (400 MHz, CDCl$_3$): 7.62-7.55 (m, 3H), 7.54 (d, J=2.0 Hz, 1H), 7.52-7.46 (m, 1H), 7.43 (d, J=8.3 Hz, 1H), 7.32-7.28 (m, 2H), 7.25 (dd, J=8.3, 2.2 Hz, 1H), 6.95-6.91 (m, 2H), 4.51 (dd, J=9.8, 5.8 Hz, 1H), 3.85 (s, 3H), 3.65 (dd, J=14.9, 9.8 Hz, 1H), 3.32 (dd, J=14.9, 5.8 Hz, 1H).

Example 28

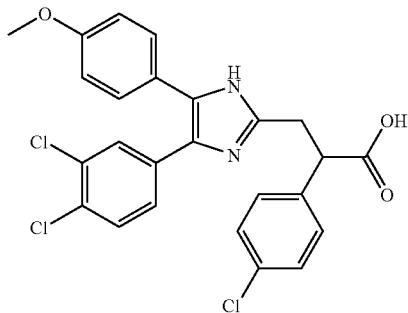

2-(4-Chloro-phenyl)-3-[4-(3,4-dichloro-phenyl)-5-(4-methoxy-phenyl)-1H-imidazol-2-yl]-propionic acid.

The title compound was prepared using the methods described in Example 24 and Scheme A substituting the olefin of Example 15 for the olefin of Example 17 (16% yield). HPLC: $R_f$=1.21 (Method D). MS (ESI): mass calculated for $C_{25}H_{19}Cl_3N_2O_3$, 500.05. m/z found, 501.0 [M+H]$^+$. $^1$H NMR (400 MHz, CDCl$_3$): 7.54 (d, J=2.2 Hz, 1H), 7.44 (d, J=8.2 Hz, 1H), 7.32 (s, 5H), 7.31-7.29 (m, 1H), 7.26 (dd, J=8.5, 2.2 Hz, 1H), 6.94 (t, J=3.0 Hz, 1H), 6.93 (t, J=3.0 Hz, 1H), 4.41 (dd, J=9.6, 6.3 Hz, 1H), 3.85 (s, 3H), 3.63 (dd, J=15.0, 9.6 Hz, 1H), 3.33 (dd, J=14.8, 6.3 Hz, 1H).

Example 29

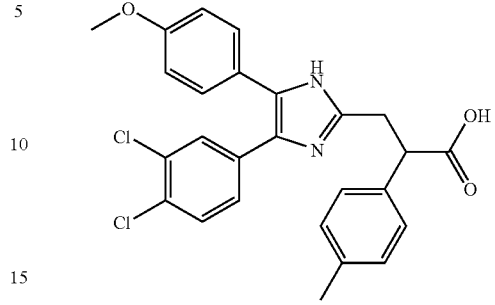

3-[4-(3,4-Dichloro-phenyl)-5-(4-methoxy-phenyl)-1H-imidazol-2-yl]-2-p-tolyl-propionic acid.

The title compound was prepared using the methods described in Example 24 and Scheme A substituting the olefin of Example 14 for the olefin of Example 17 (29% yield). HPLC: $R_f$=1.19 (Method D). MS (ESI): mass calculated for $C_{26}H_{22}Cl_2N_2O_3$, 480.10. m/z found, 481.1 [M+H]$^+$. $^1$H NMR (400 MHz, CDCl$_3$): 7.54 (d, J=2.2 Hz, 1H), 7.42 (d, J=8.3 Hz, 1H), 7.33-7.29 (m, 2H), 7.27 (dd, J=8.6, 2.2 Hz, 1H), 7.24 (d, J=8.0 Hz, 2H), 7.16 (d, J=7.8 Hz, 2H), 6.95-6.91 (m, 2H), 4.39 (dd, J=10.1, 5.8 Hz, 1H), 3.85 (s, 3H), 3.59 (dd, J=15.2, 10.1 Hz, 1H), 3.26 (dd, J=15.2, 5.8 Hz, 1H), 2.33 (s, 3H).

Example 30

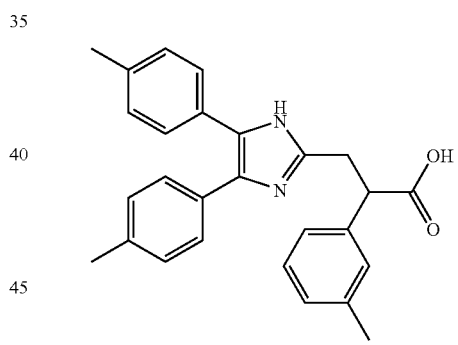

3-(4,5-Di-p-tolyl-1H-imidazol-2-yl)-2-m-tolyl-propionic acid.

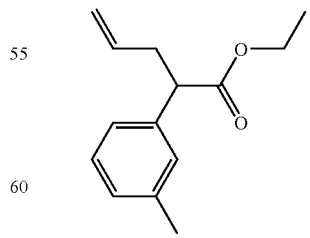

A. 2-m-Tolyl-pent-4-enoic acid ethyl ester. To a stirred solution of m-tolyl-acetic acid ethyl ester (10.0 g, 56.1 mmol) in DMF (50 mL) at 0° C. under N$_2$ was added NaH (60% dispersion in mineral oil; 2.27 g, 61.7 mmol). The reaction mixture was allowed to warm to rt and was stirred for 1.5 h. The mixture was then cooled to 0° C. and was slowly added by cannula to a solution of allyl bromide (20.4 g, 168.3 mmol) in DMF (20 mL) at −40° C. over a period of 15 min. The resulting mixture was stirred 30 min at −40° C. and was then allowed to warm to rt and stirred for 1 h. The DMF was removed under reduced pressure, and $CH_2Cl_2$ (100 mL) and $H_2O$ (100 mL) were added to the residue. The resulting layers were separated, and the organic layer was washed with brine, dried ($Na_2SO_4$), and concentrated under reduced pressure. The crude solid residue was purified on silica gel (EtOAc/hexanes) to afford the desired olefin (9.91 g, 81%). HPLC: $R_t$=10.66 (Method C). $^1H$ NMR (400 MHz, $CDCl_3$): 7.25-7.18 (m, 1H), 7.12-7.06 (m, 3H), 5.78-5.68 (m, 1H), 5.10-4.98 (m, 2H), 4.19-4.04 (m, 2H), 3.61-3.56 (m, 1H), 2.85-2.77 (m, 1H), 2.52-2.45 (m, 1H), 2.34 (s, 3H), 1.21 (t, J=7.0 Hz, 3H).

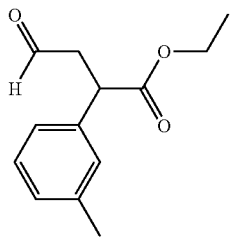

B. 4-Oxo-2-m-tolyl-butyric acid ethyl ester. A stirred solution of the olefin from Step A (1.0 g, 4.58 mmol) in 1:1 MeOH/$CH_2Cl_2$ (25 mL) was cooled to −45° C. A stream of $O_3$ (Welsbach Ozone Generator T-816-L) was bubbled through the solution until a light blue color persisted (30 min). To this solution was added dimethylsulfide (DMS; 2.85 g, 45.8 mmol), and the reaction mixture was allowed to warm to rt and was stirred for 2 h. The solvent was removed under reduced pressure, and the residue was purified on silica gel (20% EtOAc/hexanes) to afford the desired aldehyde (0.74 g, 69%). HPLC: $R_t$=2.63 (Method A). $^1H$ NMR (400 MHz, $CDCl_3$): 9.80 (s, 1H), 7.28-7.22 (m, 1H), 7.12-7.08 (m, 3H), 4.25-4.07 (m, 3H), 3.43-3.31 (m, 1H), 2.80 (dd, J=18.6, 4.7 Hz, 1H), 2.36 (s, 3H), 1.23 (t, J=7.0 Hz, 3H).

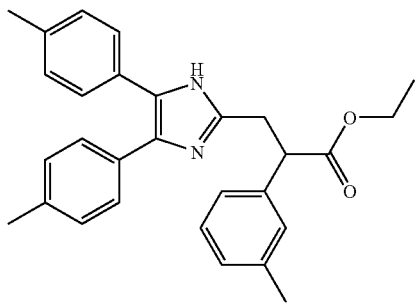

C. 3-(4,5-Di-p-tolyl-1H-imidazol-2-yl)-2-m-tolyl-propionic acid ethyl ester. The aldehyde of step B (1.91 g, 8.11 mmol) was slowly added over 4 h to a stirred solution of 4,4'-dimethylbenzil (0.48 g, 2.1 mmol) and $NH_4OAc$ (2.43 g, 31.5 mmol) in AcOH (4 mL) at 95° C. The reaction mixture was allowed to cool to rt, and the solvent was removed under reduced pressure. The residue was purified on silica gel (EtOAc/$CH_2Cl_2$) to afford the desired imidazole (0.43 g, 49%). HPLC: $R_t$=8.91 (Method C). MS (ESI): mass calculated for $C_{29}H_{30}N_2O_2$, 438.23. m/z found, 493.3 $[M+H]^+$.

D. 3-(4,5-Di-p-tolyl-1H-imidazol-2-yl)-2-m-tolyl-propionic acid. To a stirred solution of the ester from step C (50.0 mg, 0.11 mmol) in DMF (1.0 mL) was added 2 M LiOH (1.0 mL), and the reaction mixture was heated to 50° C. for 18 h. The mixture was cooled and then purified directly by reversed-phase chromatography (Method B) to afford the desired acid (41 mg, 91%). MS (ESI): mass calculated for $C_{27}H_{26}N_2O_2$, 410.20. m/z found, 411.1 $[M+H]^+$. $^1H$ NMR (400 MHz, $CDCl_3$): 7.13 (d, J=8.2 Hz, 4H), 6.97 (d, J=8.2 Hz, 4H), 6.97-6.84 (m, 4H), 4.51 (s, 1H), 3.67 (t, J=12.0 Hz, 1H), 3.35 (br d, J=12.0 Hz, 1H), 2.23 (s, 6H), 2.10 (s, 3H).

Example 31

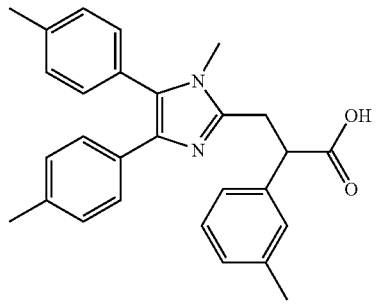

3-(1-Methyl-4,5-di-p-tolyl-1H-imidazol-2-yl)-2-m-tolyl-propionic acid. A solution of 3-(4,5-di-p-tolyl-1H-imidazol-2-yl)-2-m-tolyl-propionic acid ethyl ester (Example 30, step C; 50 mg, 0.11 mmol), iodomethane (17 mg, 0.12 mmol) and $K_2CO_3$ (79 mg, 0.55 mmol) in DMF (2.0 mL) was stirred and heated to 40° C. overnight. The solvent was removed under reduced pressure, and the crude residue was purified on silica gel (EtOAc/$CH_2Cl_2$) to give 3-(1-methyl-4,5-di-ptolyl-1H-imidazol-2-yl)-2-m-tolyl-propionic acid methyl ester (13 mg, 26%). The methyl ester (18 mg, 0.042 mmol) was hydrolyzed using the conditions outlined in Example 30, step D to provide the title compound (12 mg, 69% yield). HPLC: $R_t$=2.64 (Method A). MS (ESI): mass calculated for $C_{28}H_{28}N_2O_2$, 424.22. m/z found, 425.3 $[M+H]^+$. $^1H$ NMR (400 MHz, $CDCl_3$): 7.28-7.23 (m, 4H), 7.21-7.04 (m, 6H), 6.98 (d, J=7.8 Hz, 2H), 4;38 (d, J=9.3 Hz, 1H), 3.54 (dd, J=16.1, 9.3 Hz, 1H), 3.22 (dd, J=16.1, 3.1 Hz, 1H), 3.17 (s, 3H), 2.42 (s, 3H), 2.30 (s, 3H), 2.27 (s, 3H).

Example 32

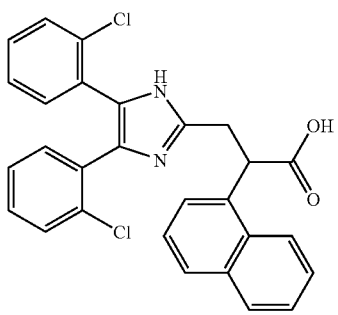

3-[4,5-Bis-(2-chloro-phenyl)-1H-imidazol-2-yl]-2-naphthalen-1-yl-propionic acid.

The title compound was prepared using the methods described in Example 30 and Scheme D substituting naphthalen-1-yl-acetic acid ethyl ester for m-tolyl-acetic acid ethyl ester in step A, and 2,2'-dichlorobenzil for 4,4'-dimethylbenzil in step C (36% yield). HPLC: $R_f$=8.07 (Method C). MS (ESI): mass calculated for $C_{28}H_{20}Cl_2N_2O_2$, 486.09. m/z found, 487.0 $[M+H]^+$. $^1$H NMR (400 MHz, CDCl$_3$): 8.11 (br s, 1H), 7.81 (d, J=8.5 Hz, 1H), 7.74 (d, J=8.5 Hz, 1H), 7.57-7.38 (m, 3H), 7.32-7.26 (m, 3H), 7.24-7.11 (m, 3H), 6.90 (br s, 3H), 5.36 (br s, 1H), 3.93 (br s, 1H), 3.74 (s, 1H).

Example 33

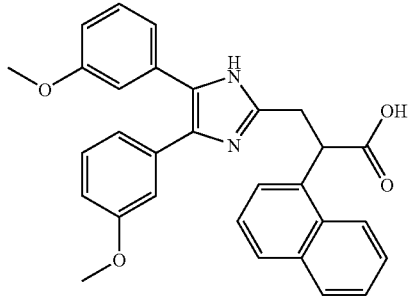

3-[4,5-Bis-(3-methoxy-phenyl)-1H-imidazol-2-yl]-2-naphthalen-1-yl-propionic acid.

The title compound was prepared using the methods described in Example 30 and Scheme D substituting naphthalen-1-yl-acetic acid ethyl ester for m-tolyl-acetic acid ethyl ester in step A, and 3,3'-dimethoxybenzil for 4,4'-dimethylbenzil in step C (30% yield). HPLC: $R_f$=8.03 (Method C). MS (ESI): mass calculated for $C_{30}H_{26}N_2O_4$, 478.19. m/z found, 479.1 $[M+H]^+$. $^1$H NMR (400 MHz, CDCl$_3$): 8.11 (d, J=8.1 Hz, 1H), 7.75 (d, J=7.8 Hz, 1H), 7.67 (d, J=8.1 Hz, 1H), 7.44-7.28 (m, 3H), 7.13 (t, J=7.3 Hz, 1H), 6.96 (t, J=7.3 Hz, 2H), 6.77-6.66 (m, 6H), 5.44 (t, J=6.0 Hz, 1H), 3.92 (dd, J=14.9, 9.6 Hz, 1H), 3.69-3.57 (m, 1H), 3.49 (s, 6H).

Example 34

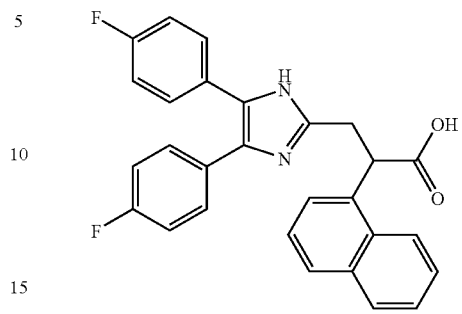

3-[4,5-Bis-(4-fluoro-phenyl)-1H-imidazol-2-yl]-2-naphthalen-1-yl-propionic acid.

The title compound was prepared using the methods described in Example 30 and Scheme D substituting naphthalen-1-yl-acetic acid ethyl ester for m-tolyl-acetic acid ethyl ester in step A, and 4,4'-diflourobenzil for 4,4'-dimethylbenzil in step C (40% yield). HPLC: $R_f$=8.14 (Method C). MS (ESI): mass calculated for $C_{28}H_{20}F_2N_2O_2$, 454.15. m/z found, 455.1 $[M+H]^+$. $^1$H NMR (400 MHz, CDCl$_3$): 8.14 (br d, J=9.0 Hz, 2H), (br d, J=7.7 Hz, 2H), (br d, J=7.7 Hz, 2H), 7.44 (br d, J=27.0 Hz, 2H), 7.16 (br s, 2H), 7.04 (br s, 2H), 6.62 (br s, 2H), 5.46 (br s, 2H), 3.81 (t, J=11.3 Hz, 2H), 3.50 (br s, 2H).

Example 35

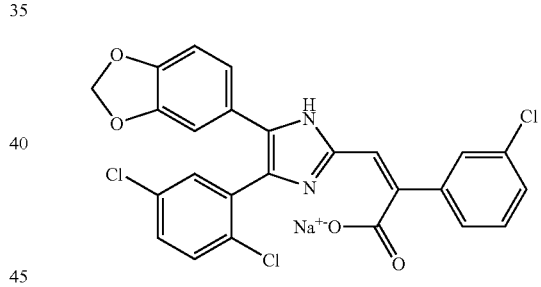

(Z)-3-[5-Benzo[1,3]dioxol-5-yl-4-(2,5-dichloro-phenyl)-1H-imidazol-2-yl]-2-(3-chloro-phenyl)-acrylic acid, sodium salt.

To a stirred solution of (Z)-3-[5-benzo[1,3]dioxol-5-yl-4-(2,5-dichloro-phenyl)-1H-imidazol-2-yl]-2-(3-chloro-phenyl)-acrylic acid (Example 1) in THF (0.2 M) is added aqueous NaOH (1 equiv) at 0° C. The mixture is stirred for 30 min at 0° C. then concentrated to an oil under reduced pressure using a rotary evaporator (25-30° C). The oil is diluted in THF (0.2 M), chilled in an ice bath, and CH$_3$CN is added to form a precipitate. The suspension is stirred for 2 h, filtered and then washed with CH$_3$CN to afford the title compound.

Assay Method

Cell Culture

CHO-K1 cells that had undergone stable transfection with the CCK-1 receptor were grown in DMEM supplemented with L-glutamine (2 mM), penicillin (50 units/mL) and streptomycin (50 μg/mL). Cells were cultured under continuous G418 selection (2 mM) and were harvested using a rubber cell scraper. CHO-K1 cells were sub-cultured a maximum of ten times before being reseeded from the original stocks.

Membrane Preparation

Membranes were prepared from the stably transfected CHO-K1 cells. Frozen cell pellets (−40° C.) were thawed in 14 mL of buffer A (10 mM HEPES, 130 mM NaCl, 4.7 mM KCl, 5 mM MgCl, 1 mM EGTA and 15.4 mg/100 mL bacitracin at pH 7.2), adapted from Harper et al. (Br. J. Pharmacol. 1996, 118:1717-1726). The thawed pellets were homogenized using a Polytron PT-10 (7×1 s). The homogenates were centrifuged for 5 min at 1500 rpm (600×g), and the resulting pellets were discarded. The supernatants were re-centrifuged in order to collect the receptor-membrane pellets (25 min 15,000 rpm; 39,800×g), which were re-suspended in buffer A.

Incubation Conditions

All assays were conducted in 96-well plates (GF/B millipore filter plates) using buffer A, with 0.3 μM PD-134,308, for the dilutions. The CCK-2 receptor ligand was included to eliminate the contribution of this receptor subtype to the binding. For the optimal cell number determination experiments 20 pM [$^{125}$I]-BH-CCK-8S (50 μL 60 pM solution) was incubated with a range of cell concentrations (2.5×105 to 12.5×105 cells/well) in a total volume of 150 μL. Total binding of [$^{125}$I]-BH-CCK-8S was determined in the presence of 15 μL of buffer A. Non-specific binding of [$^{125}$I]-BH-CCK-8S was determined in the presence of 15 μL of 100 μM 2-naphthalenesulphonyl L-aspartyl-(2-phenethyl)amide (2-NAP: see R. A. Hull et al. Br. J. Pharmacol. 1993, 108:734-740), a CCK-1 receptor selective antagonist that is structurally unrelated to the radioligand [$^{125}$I]-BH-CCK-8S. The assay preparation was incubated for 1 h at 21±3° C., and then the assay was terminated upon rapid filtration of the preparation under reduced pressure. The loaded filters were washed three times using undiluted PBS (100 μL), and then the residues were transferred to 5 mL scintillation tubes. Bound radioactivity was determined using a gamma counter (count time=1 min). From these experiments a cell concentration of 1 pellet in 40 mL of buffer (2.5×106 cells/mL) was chosen for use in other assays (below). To validate the radioligand concentration and incubation time for the assay, saturation and kinetic binding studies were also conducted (see M. F. Morton, The Pharmacological Characterization of Cholecystokinin Receptors in the Human Gastrointestinal Tract. PhD Thesis, University of London, 2000). The affinity of novel compounds was estimated by incubating membrane preparations with 15 μL of competing ligand (0.1 pM-1 mM) for 60 min at 21±3° C. The assay was then terminated according to the procedure outlined above.

Data Analysis

The pKi values were determined using the equation of Y.-C. Cheng and W. H. Prusoff (Biochem. Pharmacol. 1973, 22(23):3099-3108):

$$K_i = \frac{IC_{50}}{1 + \frac{[L]}{K_D}}$$

To circumvent problems associated with computer-assisted data analysis of compounds with low affinity, the data obtained in the current study were weighted according to a method described by Morton (2000). In brief, 100% and 0% specific binding were defined independently using total binding and binding obtained in the presence of a high concentration of the reference antagonist, 2-NAP.

TABLE

| EX | pK$_i$ |
|----|--------|
| 1  | 8.7 |
| 2  | 8.5 |
| 3  | 8.7 |
| 4  | 8.6 |
| 5  | 8.5 |
| 6  | 8.4 |
| 7  | 8.3 |
| 8  | 8.3 |
| 9  | 8.1 |
| 10 | 8.0 |
| 11 | 8.0 |
| 12 | 8.3 |
| 13 | 6.7 |
| 14 | 7.0 |
| 15 | 7.1 |
| 16 | 7.1 |
| 17 | 7.1 |
| 18 | 7.2 |
| 19 | 7.8 |
| 20 | 7.8 |
| 21 | 7.7 |
| 22 | 7.6 |
| 23 | 7.1 |
| 24 | 7.5 |
| 25 | 7.5 |
| 26 | 7.4 |
| 27 | 7.3 |
| 28 | 7.2 |
| 29 | 6.9 |
| 30 | 7.7 |
| 31 | 7.4 |
| 32 | 6.4 |
| 33 | 5.6 |
| 34 | 5.0 |

Having described the invention in specific detail and exemplified the manner in which it may be carried into practice, it will be apparent to those skilled in the art that innumerable variations, applications, modifications, and extensions of the basic principles involved may be made without departing from its spirit or scope. It is to be understood that the foregoing is merely exemplary and the present invention is not to be limited to the specific form or arrangements of parts herein described and shown.

What is claimed is:

1. A compound having CCK1 receptor modulating activity of formula (I):

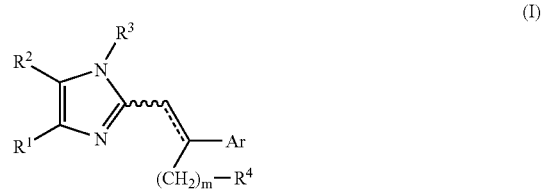

(I)

wherein,

R$^1$ and R$^2$ can be the same or different and are selected from the group consisting of;

a) phenyl, optionally mono-, di- or tri-substituted with R$^p$ or di-substituted on adjacent carbons with —OC$_{1-4}$ alkyleneO—, —(CH$_2$)$_{2-3}$NH—, —

$-(CH_2)_{1-2}NH(CH_2)-$, $-(CH_2)_{2-3}N(C_{1-4}alkyl)$- or $-(CH_2)_{1-2}N(C_{1-4}alkyl)(CH_2)-$;

$R^p$ is selected from the group consisting of —OH, —$C_{1-6}$alkyl, —$OC_{1-6}$alkyl, phenyl, —Ophenyl, benzyl, —Obenzyl, —$C_{3-6}$cycloalkyl, —$OC_{3-6}$cycloalkyl, —CN, —$NO_2$, —$N(R^y)R^z$ (wherein $R^y$ and $R^z$ are independently selected from —H, —$C_{1-6}$alkyl or —$C_{1-6}$alkenyl, or $R^y$ and $R^z$ may be taken together with the nitrogen of attachment to form an otherwise aliphatic hydrocarbon ring, said ring having 4 to 7 members, optionally having one carbon replaced with >O, =N—, >NH or >$N(C_{1-4}$ alkyl), optionally having one carbon substituted with —OH, and optionally having one or two double bonds in the ring), —(C=O)$N(R^y)R^z$, —(N—$R^t$)$COR^t$, —(N—$R^t$)$SO_2C_{1-6}$alkyl (wherein $R^t$ is —H or —$C_{1-6}$alkyl or two $R^t$ in the same substituent may be taken together with the amide of attachment to form an otherwise aliphatic hydrocarbon ring, said ring having 4 to 6 members), —(C=O)$C_{1-6}$alkyl, —(S=(O)$_n$)—$C_{1-6}$ alkyl (wherein n is selected from 0, 1 or 2), —$SO_2N(R^y)R^z$, —$SCF_3$, halo, —$CF_3$, —$OCF_3$, —COOH and —$COOC_{1-6}$alkyl;

b) phenyl or pyridyl fused at two adjacent ring members to a three membered hydrocarbon moiety to form a fused five membered aromatic ring, which moiety has one carbon atom replaced by >O, >S, >NH or >$N(C_{1-4}$alkyl) and which moiety has up to one additional carbon atom optionally replaced by N, the fused rings optionally mono-, di- or tri-substituted with $R^p$;

c) phenyl fused at two adjacent ring members to a four membered hydrocarbon moiety to form a fused six membered aromatic ring, which moiety has one or two carbon atoms replaced by N, the fused rings optionally mono-, di- or tri-substituted with $R^p$;

d) naphthyl, optionally mono-, di- or tri-substituted with $R^p$;

e) a monocyclic aromatic hydrocarbon group having five ring atoms, having a carbon atom which is the point of attachment, having one carbon atom replaced by >O, >S, >NH or >$N(C_{1-4}$alkyl), having up to one additional carbon atoms optionally replaced by N, optionally mono- or di-substituted with $R^p$ and optionally benzo fused, where the benzo fused moiety is optionally mono-, di- or tri-substituted with $R^p$; and f) a monocyclic aromatic hydrocarbon group having six ring atoms, having a carbon atom which is the point of attachment, having one or two carbon atoms replaced by N, having one N optionally oxidized to the N-oxide, optionally mono- or di-substituted with $R^p$ and optionally benzo fused, where the benzo fused moiety is optionally mono- or di-substituted with $R^p$;

$R^3$ is selected from the group consisting of —H and —$C_{1-6}$alkyl;

m is selected from 0, 1, or 2;

Ar is selected from the group consisting of:

A) phenyl, optionally mono-, di- or tri-substituted with $R^r$ or di-substituted on adjacent carbons with —$OC_{1-4}$ alkyleneO—, —$(CH_2)_{2-3}NH$—, —$(CH_2)_{1-2}NH(CH_2)$—, —$(CH_2)_{2-3}N(C_{1-4}alkyl)$- or —$(CH_2)_{1-2}N(C_{1-4}alkyl)(CH_2)$—;

$R^r$ is selected from the group consisting of —OH, —$C_{1-6}$alkyl, —$OC_{1-6}$alkyl, phenyl, —Ophenyl, benzyl, —Obenzyl, —$C_{3-6}$cycloalkyl, —$OC_{3-6}$cycloalkyl, —CN, —$NO_2$, —$N(R^a)R^b$ (wherein $R^a$ and $R^b$ are independently selected from —H, —$C_{1-6}$alkyl or —$C_{1-6}$alkenyl, or $R^a$ and $R^b$ may be taken together with the nitrogen of attachment to form an otherwise aliphatic hydrocarbon ring, said ring having 4 to 7 members, optionally having one carbon replaced with >O, =N—, >NH or >$N(C_{1-4}$ alkyl), optionally having one carbon substituted with —OH, and optionally having one or two double bonds in the ring), —(C=O)$N(R^a)R^b$, —(N—$R^c$)$COR^c$, —(N—$R^c$)$SO_2C_{1-6}$alkyl (wherein $R^c$ is H or $C_{1-6}$alkyl or two $R^c$ in the same substituent may be taken together with the amide of attachment to form an otherwise aliphatic hydrocarbon ring, said ring having 4 to 6 members), —(C=O)$C_{1-6}$alkyl, —(S=(O)$_q$)—$C_{1-6}$ alkyl (wherein q is selected from 0, 1 or 2), —$SO_2N(R^a)R^b$, —$SCF_3$, halo, —$CF_3$, —$OCF_3$, and —$COOC_{1-6}$alkyl;

B) phenyl or pyridyl fused at two adjacent ring members to a three membered hydrocarbon moiety to form a fused five membered aromatic ring, which moiety has one carbon atom replaced by >O, >S, >NH or >$N(C_{1-4}$ alkyl) and which moiety has up to one additional carbon atom optionally replaced by N, the fused rings optionally mono-, di- or tri-substituted with $R^r$;

C) phenyl fused at two adjacent ring members to a four membered hydrocarbon moiety to form a fused six membered aromatic ring, which moiety has one or two carbon atoms replaced by N, the fused rings optionally mono-, di- or tri-substituted with $R^r$;

D) naphthyl, optionally mono-, di- or tri-substituted with $R^r$;

E) a monocyclic aromatic hydrocarbon group having five ring atoms, having a carbon atom which is the point of attachment, having one carbon atom replaced by >O, >S, >NH or >$N(C_{1-4}$alkyl), having up to one additional carbon atoms optionally replaced by N, optionally mono- or di-substituted with $R^r$ and optionally benzo fused on the condition that two or fewer of said carbon ring atoms are replaced by a heteroatom, where the benzo fused moiety is optionally mono-, di- or tri-substituted with $R^r$; and F) a monocyclic aromatic hydrocarbon group having six ring atoms, having a carbon atom which is the point of attachment, having one or two carbon atoms replaced by N, optionally mono- or di-substituted with $R^r$ and optionally benzo fused, where the benzo fused moiety is optionally mono- or di-substituted with $R^r$;

$R^4$ is selected from the group consisting of;

I) —$COOR^5$, where $R^5$ is selected from the group consisting of —H and —$C_{1-4}$alkyl, and II) —$CONR^6R^7$, where $R^6$ and $R^7$ are independently selected from the group consisting of —H, —$C_{1-6}$ alkyl and —$C_{3-6}$cycloalkyl optionally hydroxy substituted, or $R^6$ and $R^7$ may be taken together with the nitrogen of attachment to form an otherwise aliphatic hydrocarbon ring, said ring having 5 to 7 members, optionally having one carbon replaced with >O, =N—, >NH or >$N(C_{1-4}$alkyl) and optionally having one or two double bonds in the ring;

and enantiomers, diastereomers, hydrates, solvates and pharmaceutically acceptable salts, esters and amides thereof.

2. The compound of claim 1 wherein $R^1$ and $R^2$, optionally substituted, are selected from the group consisting of:

a) phenyl, 5-, 6-, 7-, 8-benzo-1,4-dioxanyl, 4-, 5-, 6-, 7-benzo-1,3-dioxolyl, 4-, 5-, 6-, 7-indolinyl, 4-, 5-, 6-, 7-isoindolinyl, 1,2,3,4-tetrahydro-quinolin-4, 5, 6 or 7-yl, 1,2,3,4-tetrahydro-isoquinolin-4, 5, 6 or 7-yl,
b) 4-, 5-, 6- or 7-benzoxazolyl, 4-, 5-, 6- or 7-benzothiophenyl, 4-, 5-, 6- or 7-benzofuranyl, 4-, 5-, 6- or 7-indolyl, 4-, 5-, 6- or 7-benzthiazolyl, 4-, 5-, 6- or 7-benzimidazolyl, 4-, 5-, 6- or 7-indazolyl, imidazo[1,2-a]pyridin-5, 6, 7 or 8-yl, pyrazolo[1,5-a]pyridin-4, 5, 6 or 7-yl, 1H-pyrrolo[2,3-b]pyridin-4, 5 or 6-yl, 1H-pyrrolo[3,2-c]pyridin-4, 6 or 7-yl, 1H-pyrrolo[2,3-c]pyridin-4, 5 or 7-yl, 1H-pyrrolo[3,2-b]pyridin-5, 6 or 7-yl,
c) 5-, 6-, 7- or 8-isoquinolinyl, 5-, 6-, 7- or 8-quinolinyl, 5-, 6-, 7- or 8-quinoxalinyl, 5-, 6-, 7- or 8-quinazolinyl,
d) naphthyl,
e) furanyl, oxazolyl, isoxazolyl, thiophenyl, thiazolyl, isothiazolyl, pyrrolyl, imidazolyl, pyrazolyl, 3-indoxazinyl, 2-benzoxazolyl, 2- or 3-benzothiophenyl, 2- or 3-benzofuranyl, 2- or 3-indolyl, 2-benzthiazolyl, 2-benzimidazolyl, or 3-indazolyl,
f) pyridinyl, pyridinyl-N-oxide, pyrazinyl, pyrimidinyl, pyridazinyl, 1-, 3- or 4-isoquinolinyl, 2-, 3- or 4-quinolinyl, 2- or 3-quinoxalinyl, 2- or 4-quinazolinyl, and 1-oxy-pyridin-2, 3, or 4-yl.

3. The compound of claim 1 wherein $R^1$ and $R^2$ can be the same or different and optionally substituted, and are selected from the group consisting of phenyl, pyridinyl, and naphthyl.

4. The compound of claim 1 wherein $R^1$ and $R^2$ can be the same or different and optionally substituted, and are selected from the group consisting of phenyl, 2-methoxy-phenyl, 3-methoxy-phenyl, 4-methoxy-phenyl, 2,3-dimethoxy-phenyl, 2,4-dimethoxy-phenyl, 3,4-dimethoxy-phenyl, 2-chloro-phenyl, 3-chloro-phenyl, 4-chloro-phenyl, 2,3-dichloro-phenyl, 2,4-dichloro-phenyl, 3,4-dichlorophenyl, 2,5-dichloro-phenyl, 2-fluoro-phenyl, 3-fluoro-phenyl, 4-fluoro-phenyl, 2-methyl-phenyl, 3-methyl-phenyl, 4-methyl-phenyl, 2,5-dimethyl-phenyl, 2-trifluoromethyl-phenyl, 3-trifluoromethyl-phenyl, 4-trifluoromethyl-phenyl, 3-trifluoromethoxy-phenyl, 4-trifluoromethoxy-phenyl, 4-t-butyl-phenyl, naphthalen-2-yl, naphthalen-1-yl, pyridin-2-yl, pyridin-3-yl, pyridin-4-yl, 4-methanesulfonyl-phenyl, 4-isopropyl-phenyl, 4-ethoxy-phenyl, 4-hydroxy-phenyl, benzo[1,3]diox-5-yl, and 2,3-dihydro benzo[1,4]dioxin-6-yl.

5. The compound of claim 1 wherein $R^p$ is selected from the group consisting of —OH, —CH$_3$, —CH$_2$CH$_3$, i-propyl, t-butyl, —OCH$_3$, —OCH$_2$CH$_3$, —OCH(CH$_3$)$_2$, phenyl, —Ophenyl, benzyl, —Obenzyl, cyclopropyl, cyclobutyl, cyclopentyl, cyclohexyl, —Ocyclopentyl, —Ocyclohexyl, —CN, —NO$_2$, —NH$_2$, —NHCH$_3$, —NHCH$_2$CH$_3$, —NH(CH$_2$CH$_2$CH$_3$), —NH(CH(CH$_3$)CH$_2$CH$_3$), —NH(allyl), —NH(CH$_2$(CH$_3$)$_2$), —N(CH$_3$)$_2$, —N(CH$_2$CH$_3$)$_2$, —NCH$_3$(CH$_2$CH$_2$CH$_3$), —NCH$_3$(CH$_2$CH$_3$), —NCH$_3$(CH(CH$_3$)$_2$), pyrrolidin-2-on-1-yl, azetidinyl, piperidin-1-yl, 2- or 3-pyrrolin-1-yl, morpholin-4-yl, thiomorpholin-4-yl, piperazin-1-yl, pyrrolidin-1-yl, homopiperidin-1-yl, —C(O)NH$_2$, —C(O)N(CH$_3$)$_2$, —C(O)NH(CH$_3$), —NH(CO)H, —NHCOCH$_3$, —NCH$_3$(CO)H, —NCH$_3$COCH$_3$, —NHSO$_2$CH$_3$, —NCH$_3$SO$_2$CH$_3$, —C(O)CH$_3$, —SOCH$_3$, —SO$_2$CH$_3$, —SO$_2$NH$_2$, —SO$_2$NHCH$_3$, —SO$_2$N(CH$_3$)$_2$, —SCF$_3$, —F, —Cl, —Br, —I, —CF$_3$, —OCF$_3$, —COOH, —COOCH$_3$, and —COOCH$_2$CH$_3$.

6. The compound of claim 1 wherein $R^p$ is selected from the group consisting of —CH$_3$, —OCH$_3$, —OCH$_2$CH$_3$, —Cl, —F, —CF$_3$, —OCF$_3$, t-butyl, —SO$_2$CH$_3$, i-propyl and —OH.

7. The compound of claim 1 wherein $R^3$ is selected from the group consisting of —H, —CH$_3$, —CH$_2$CH$_3$, —CH$_2$CH$_2$CH$_3$, and —CH(CH$_3$)$_2$.

8. The compound of claim 1 wherein $R^3$ is —H or —CH$_3$.

9. The compound of claim 1 wherein m is 0.

10. The compound of claim 1 wherein the Ar attached carbon is saturated and has the configuration

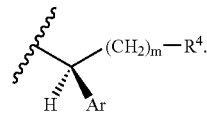

11. The compound of claim 1 wherein the Ar attached carbon is saturated and has the configuration

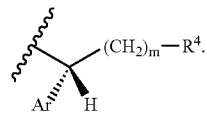

12. The compound of claim 1 wherein the Ar attached carbon is unsaturated and has the configuration

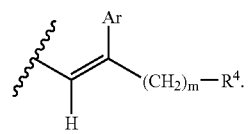

13. The compound of claim 1 wherein the Ar attached carbon is unsaturated and has the configuration

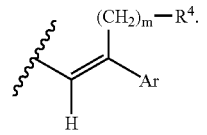

14. The compound of claim 1 wherein Ar, optionally substituted, is selected from the group consisting of:
A) phenyl, 5-, 6-, 7-, 8-benzo-1,4-dioxanyl, 4-, 5-, 6-, 7-benzo-1,3-dioxolyl, 4-, 5-, 6-, 7-indolinyl, 4-, 5-, 6-, 7-isoindolinyl, 1,2,3,4-tetrahydro-quinolin-4, 5, 6 or 7-yl, 1,2,3,4-tetrahydro-isoquinolin-4, 5, 6 or 7-yl,
B) 4-, 5-, 6- or 7-benzoxazolyl, 4-, 5-, 6- or 7-benzothiophenyl, 4-, 5-, 6- or 7-benzofuranyl, 4-, 5-, 6- or 7-indolyl, 4-, 5-, 6- or 7-benzthiazolyl, 4-, 5-, 6- or 7-benzimidazolyl, 4-, 5-, 6- or 7-indazolyl, imidazo[1,2-a]pyridin-5, 6, 7 or 8-yl, pyrazolo[1,5-a]pyridin-4, 5, 6 or 7-yl, 1H-pyrrolo[2,3-b]pyridin-4, 5 or 6-yl, 1H-pyrrolo[3,2-c]pyridin-4, 6 or 7-yl, 1H-pyrrolo[2,3-c]pyridin-4, 5 or 7-yl, 1H-pyrrolo[3,2-b]pyridin-5, 6 or 7-yl,
C) 5-, 6-, 7- or 8-isoquinolinyl, 5-, 6-, 7- or 8-quinolinyl, 5-, 6-, 7- or 8-quinoxalinyl, 5-, 6-, 7- or 8-quinazolinyl,
D) naphthyl,
E) furanyl, oxazolyl, isoxazolyl, thiophenyl, thiazolyl, isothiazolyl, pyrrolyl, imidazolyl, pyrazolyl, 3-indoxazinyl, 2-benzoxazolyl, 2- or 3-benzothiophenyl, 2- or 3-benzofuranyl, 2- or 3-indolyl, 2-benzthiazolyl, 2-benzimidazolyl, or 3-indazolyl, F) pyridinyl, pyrazinyl, pyrimidinyl, pyridazinyl, 1-, 3- or 4-isoquinolinyl, 2-, 3- or 4-quinolinyl, 2- or 3-quinoxalinyl, 2- or 4-quinazolinyl.

15. The compound of claim 1 wherein Ar, optionally substituted, is selected from the group consisting of phenyl, naphthyl, benzofuran-3-yl, 4-, 5-, 6- or 7-benzothiophenyl, 4-, 5-, 6- or 7-benzo[1,3]dioxolyl, 8-quinolinyl, 2-indolyl, 3-indolyl and pyridinyl.

16. The compound of claim 1 wherein Ar, optionally substituted, is phenyl or naphthyl.

17. The compound of claim 1 wherein Ar is selected from the group consisting of phenyl, 2-methyl-phenyl, 3-methyl-phenyl, 4-methyl-phenyl, 2,5-dimethyl-phenyl, 2-trifluoromethyl-phenyl, 3-trifluoromethyl-phenyl, 4-trifluoromethyl-phenyl, 2-fluoro-3-trifluoromethyl-phenyl, 2-fluoro-phenyl, 3-fluoro-phenyl, 4-fluoro-phenyl, 2,3-difluoro-phenyl, 2-chloro-phenyl, 3-chloro-phenyl, 4-chloro-phenyl 2,3-dichloro-phenyl, 3,4-dichlorophenyl, 2,6-dichlorophenyl, 3-iodo-phenyl, 2-chloro-4-fluoro-phenyl, benzofuran-3-yl, 2-methoxy-phenyl, 3-methoxy-phenyl, 4-methoxy-phenyl, 2,3-dimethoxy-phenyl, 3-trifluoromethoxy-phenyl, 4-trifluoromethoxy-phenyl, 3-ethoxy-phenyl, 3-trifluoromethylsulfanyl-phenyl, naphthalen-1-yl, naphthalen-2-yl, benzo[b]thiophen-4-yl, 3-nitro-phenyl, benzo[1,3]dioxol-5-yl, pyridin-3-yl, pyridin-4-yl, 3-indolyl, 1-methyl-indol-3-yl, 4-biphenyl, 3,5-dimethyl-phenyl, 3-isopropoxy-phenyl, 3-dimethylamino-phenyl, 2-flouro-5-methyl-phenyl, and 2-methyl-3-trifluoromethyl-phenyl.

18. The compound of claim 1 wherein there are 0, 1 or 2 $R^r$ substituents.

19. The compound of claim 1 wherein $R^r$ is selected from the group consisting of —OH, —CH$_3$, —CH$_2$CH$_3$, -propyl, -t-butyl, —OCH$_3$, —OCH$_2$CH$_3$, —OCH(CH$_3$)$_2$, phenyl, —Ophenyl, benzyl, —Obenzyl, cyclopentyl, cyclohexyl, —Ocyclopentyl, —Ocyclohexyl, —CN, —NO$_2$, —NH$_2$, —N(CH$_3$)$_2$, —N(CH$_2$CH$_3$)$_2$, pyrrolidin-2-on-1-yl, piperidin-1-yl, 2- or 3-pyrrolin-1-yl, morpholin-4-yl, thiomorpholin-4-yl, piperazin-1-yl, pyrrolidin-1-yl, —C(O)NH$_2$, —C(O)N(CH$_3$)$_2$, —C(O)NH(CH$_3$), —NHCOCH$_3$, —NHSO$_2$CH$_3$, —C(O)CH$_3$, —SOCH$_3$, —SO$_2$CH$_3$, —SO$_2$N(CH$_3$)$_2$, —SCF$_3$, —F, —Cl, —Br, —I, —CF$_3$, —OCF$_3$, and —COOCH$_3$.

20. The compound of claim 1 wherein $R^r$ is selected from the group consisting of —CH$_3$, —OCH$_3$, —OCH$_2$CH$_3$, —OCH(CH$_3$)$_2$, —F, —Cl, —Br, —CF$_3$, and —OCF$_3$.

21. The compound of claim 1 wherein $R^4$ is selected from the group consisting of:
I) —COOH, —COOCH$_3$, —COOCH$_2$CH$_3$,
II) —CONH(CH$_3$), —CONH(CH$_2$CH$_3$), —CONH(CH$_2$CH$_2$CH$_3$), —CONH(CH(CH$_3$)$_2$), —CONH(CH$_2$CH$_2$CH$_2$CH$_3$), —CONH(CH(CH$_3$)CH$_2$CH$_3$), —CONH(C(CH$_3$)$_3$), —CONH(cyclohexyl), —CONH(2-hydroxy-cyclohexyl), —CON(CH$_3$)$_2$, —CONCH$_3$(CH$_2$CH$_3$), —CONCH$_3$(CH$_2$CH$_2$CH$_3$), —CONCH$_3$(CH(CH$_3$)$_2$), —CONCH$_3$(CH$_2$CH$_2$CH$_2$CH$_3$), —CONCH$_3$(CH(CH$_3$)CH$_2$CH$_3$), —CONCH$_3$(C(CH$_3$)$_3$), —CON(CH$_2$CH$_3$)$_2$, —CO-piperidin-1-yl, —CO-morpholin-4-yl, —CO-piperazin-1-yl, —CO-pyrrolidin-1-yl, —CO-2-pyrrolin-1-yl, —CO-3-pyrrolin-1-yl, and —CO-piperidin-1-yl.

22. The compound of claim 1 wherein $R^4$ is —COOH.

23. The compound of claim 1 wherein said pharmaceutically acceptable salt is an amino addition salt.

24. The compound of claim 1 wherein said pharmaceutically acceptable salt is an acid addition salt.

25. The compound of claim 1 wherein said pharmaceutically acceptable salt is selected from the group consisting of hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate.

26. The compound of claim 1 wherein said pharmaceutically acceptable salt is selected from the group consisting of sodium, potassium, calcium, magnesium, ammonium, quaternary ammonium, tetramethyl ammonium, methylammonium, trimethylammonium, and ethylammonium.

27. The compound of claim 1 selected from the group consisting of:
(Z)-3-[5-Benzo[1,3]dioxol-5-yl-4-(2,5-dichloro-phenyl)-1H-imidazol-2-yl]-2-(3-chloro-phenyl)-acrylic acid;
(E)-3-[5-Benzo[1,3]dioxol-5-yl-4-(2,5-dichloro-phenyl)-1H-imidazol-2-yl]-2-(3-chloro-phenyl)-acrylic acid;
(Z)-3-[5-Benzo[1,3]dioxol-5-yl-4-(2,5-dichloro-phenyl)-1H-imidazol-2-yl]-2-m-tolyl-acrylic acid;
(Z)-3-[5-Benzo[1,3]dioxol-5-yl-4-(2,5-dichloro-phenyl)-1H-imidazol-2-yl]-2-naphthalen-1-yl-acrylic acid;
(Z)-3-[5-Benzo[1,3]dioxol-5-yl-4-(2,5-dichloro-phenyl)-1H-imidazol-2-yl]-2-(4-chloro-phenyl)-acrylic acid;
(Z)-3-[5-Benzo[1,3]dioxol-5-yl-4-(2,5-dichloro-phenyl)-1H-imidazol-2-yl]-2-p-tolyl-acrylic acid;
(Z)-3-[5-Benzo[1,3]dioxol-5-yl-4-(2,5-dichloro-phenyl)-1H-imidazol-2-yl]-2-(3-trifluoromethyl-phenyl)-acrylic acid;
(Z)-2-(3-Chloro-phenyl)-3-[4-(3,4-dichloro-phenyl)-5-(4-methoxy-phenyl)-1H-imidazol-2-yl]-acrylic acid;
(Z)-3-[4-(3,4-Dichloro-phenyl)-5-(4-methoxy-phenyl)-1H-imidazol-2-yl]-2-m-tolyl-acrylic acid;
(Z)-3-[4-(3,4-Dichloro-phenyl)-5-(4-methoxy-phenyl)-1H-imidazol-2-yl]-2-(3-trifluoromethyl-phenyl)-acrylic acid;
(Z)-3-[4-(3,4-Dichloro-phenyl)-5-(4-methoxy-phenyl)-1H-imidazol-2-yl]-2-p-tolyl-acrylic acid;
(Z)-2-(3-Chloro-phenyl)-3-(5-naphthalen-2-yl-4-pyridin-2-yl-1H-imidazol-2-yl)-acrylic acid;
(E)-3-[4-(3,4-Dichloro-phenyl)-5-(4-methoxy-phenyl)-1H-imidazol-2-yl]-2-naphthalen-1-yl-acrylic acid;
(E)-3-[4-(3,4-Dichloro-phenyl)-5-(4-methoxy-phenyl)-1H-imidazol-2-yl]-2-p-tolyl-acrylic acid;
(E)-2-(4-Chloro-phenyl)-3-[4-(3,4-dichloro-phenyl)-5-(4-methoxy-phenyl)-1H-imidazol-2-yl]-acrylic acid;
(E)-3-[4-(3,4-Dichloro-phenyl)-5-(4-methoxy-phenyl)-1H-imidazol-2-yl]-2-(3-trifluoromethyl-phenyl)-acrylic acid;
(E)-3-[4-(3,4-Dichloro-phenyl)-5-(4-methoxy-phenyl)-1H-imidazol-2-yl]-2-m-tolyl-acrylic acid;
(E-2-(3-Chloro-phenyl)-3-[4-(3,4-dichloro-phenyl)-5-(4-methoxy-phenyl)-1H-imidazol-2-yl]-acrylic acid;
(E)-3-[5-Benzo[1,3]dioxol-5-yl-4-(2,5-dichloro-phenyl)-1H-imidazol-2-yl]-2-m-tolyl-acrylic acid;
(E)-3-[5-Benzo[1,3]dioxol-5-yl-4-(2,5-dichloro-phenyl)-1H-imidazol-2-yl]-2-(4-chloro-phenyl)-acrylic acid;
(E)-3-[5-Benzo[1,3]dioxol-5-yl-4-(2,5-dichloro-phenyl)-1H-imidazol-2-yl]-2-(3-trifluoromethyl-phenyl)-acrylic acid;
(E)-3-[5-Benzo[1,3]dioxol-5-yl-4-(2,5-dichloro-phenyl)-1H-imidazol-2-yl]-2-p-tolyl-acrylic acid;
(E)-3-[5-Benzo[1,3]dioxol-5-yl-4-(2,5-dichloro-phenyl)-1H-imidazol-2-yl]-2-naphthalen-1-yl-acrylic acid;
3-[4-(3,4-Dichloro-phenyl)-5-(4-methoxy-phenyl)-1H-imidazol-2-yl]-2-m-tolyl-propionic acid;

2-(3-Chloro-phenyl)-3-[4-(3,4-dichloro-phenyl)-5-(4-methoxy-phenyl)-1H-imidazol-2-yl]-propionic acid;
3-[4-(3,4-Dichloro-phenyl)-5-(4-methoxy-phenyl)-1H-imidazol-2-yl]-2-naphthalen-1-yl-propionic acid;
3-[4-(3,4-Dichloro-phenyl)-5-(4-methoxy-phenyl)-1H-imidazol-2-yl]-2-(3-trifluoromethyl-phenyl)-propionic acid;
2-(4-Chloro-phenyl)-3-[4-(3,4-dichloro-phenyl)-5-(4-methoxy-phenyl)-1H-imidazol-2-yl]-propionic acid;
3-[4-(3,4-Dichloro-phenyl)-5-(4-methoxy-phenyl)-1H-imidazol-2-yl]-2-p-tolyl-propionic acid;
3-(4,5-Di-p-tolyl-1H-imidazol-2-yl)-2-m-tolyl-propionic acid;
3-(1-Methyl-4,5-di-p-tolyl-1H-imidazol-2-yl)-2-m-tolyl-propionic acid;
3-[4,5-Bis-(2-chloro-phenyl)-1H-imidazol-2-yl]-2-naphthalen-1-yl-propionic acid;
3-[4,5-Bis-(3-methoxy-phenyl)-1H-imidazol-2-yl]-2-naphthalen-1-yl-propionic acid;
3-[4,5-Bis-(4-fluoro-phenyl)-1H-imidazol-2-yl]-2-naphthalen-1-yl-propionic acid; and
(Z)-3-[5-Benzo[1,3]dioxol-5-yl-4-(2,5-dichloro-phenyl)-1H-imidazol-2-yl]-2-(3-chloro-phenyl)-acrylic acid, sodium salt.

28. A pharmaceutical composition comprising a pharmaceutically acceptable carrier and a therapeutically effective amount of compound having CCK1 receptor modulating activity of formula (I):

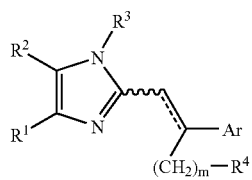

(I)

wherein,
$R^1$ and $R^2$ can be the same or different and are selected from the group consisting of;
a) phenyl, optionally mono-, di- or tri-substituted with $R^p$ or di-substituted on adjacent carbons with —$OC_{1-4}$ alkyleneO—, —$(CH_2)_{2-3}NH$—, —$(CH_2)_{1-2}NH(CH_2)$—, —$(CH_2)_{2-3}N(C_{1-4}alkyl)$- or —$(CH_2)_{1-2}N(C_{1-4}alkyl)(CH_2)$—;
$R^p$ is selected from the group consisting of —OH, —$C_{1-6}$alkyl, —$OC_{1-6}$alkyl, phenyl, —Ophenyl, benzyl, —Obenzyl, —$C_{3-6}$cycloalkyl, —$OC_{3-6}$cycloalkyl, —CN, —$NO_2$, —$N(R^y)R^z$ (wherein $R^y$ and $R^z$ are independently selected from —H, —$C_{1-6}$alkyl or —$C_{1-6}$alkenyl, or $R^y$ and $R^z$ may be taken together with the nitrogen of attachment to form an otherwise aliphatic hydrocarbon ring, said ring having 4 to 7 members, optionally having one carbon replaced with >O, =N—, >NH or >N($C_{1-4}$alkyl), optionally having one carbon substituted with —OH, and optionally having one or two double bonds in the ring), —(C=O)N($R^y$)$R^z$, —(N—$R^t$)COR$^t$, —(N—$R^t$)$SO_2C_{1-6}$alkyl (wherein $R^t$ is —H or —$C_{1-6}$alkyl or two $R^t$ in the same substituent may be taken together with the amide of attachment to form an otherwise aliphatic hydrocarbon ring, said ring having 4 to 6 members), —(C=O)$C_{1-6}$alkyl, —(S=(O)$_n$)—$C_{1-6}$ alkyl (wherein n is selected from 0, 1 or 2), —$SO_2N(R^y)R^z$, —$SCF_3$, halo, —$CF_3$, —$OCF_3$, —COOH and —$COOC_{1-6}$alkyl;
b) phenyl or pyridyl fused at two adjacent ring members to a three membered hydrocarbon moiety to form a fused five membered aromatic ring, which moiety has one carbon atom replaced by >O, >S, >NH or >N($C_{1-4}$alkyl) and which moiety has up to one additional carbon atom optionally replaced by N, the fused rings optionally mono-, di- or tri-substituted with $R^p$;
c) phenyl fused at two adjacent ring members to a four membered hydrocarbon moiety to form a fused six membered aromatic ring, which moiety has one or two carbon atoms replaced by N, the fused rings optionally mono-, di- or tri-substituted with $R^p$;
d) naphthyl, optionally mono-, di- or tri-substituted with $R^p$;
e) a monocyclic aromatic hydrocarbon group having five ring atoms, having a carbon atom which is the point of attachment, having one carbon atom replaced by >O, >S, >NH or >N($C_{1-4}$alkyl), having up to one additional carbon atoms optionally replaced by N, optionally mono- or di-substituted with $R^p$ and optionally benzo fused, where the benzo fused moiety is optionally mono-, di- or tri-substituted with $R^p$; and
f) a monocyclic aromatic hydrocarbon group having six ring atoms, having a carbon atom which is the point of attachment, having one or two carbon atoms replaced by N, having one N optionally oxidized to the N-oxide, optionally mono- or di-substituted with $R^p$ and optionally benzo fused, where the benzo fused moiety is optionally mono- or di-substituted with $R^p$;
$R^3$ is selected from the group consisting of —H and —$C_{1-6}$alkyl;
m is selected from 0, 1, or 2;
Ar is selected from the group consisting of:
A) phenyl, optionally mono-, di- or tri-substituted with $R^r$ or di-substituted on adjacent carbons with —$OC_{1-4}$ alkyleneO—, —$(CH_2)_{2-3}NH$—, —$(CH_2)_{1-2}NH(CH_2)$—, —$(CH_2)_{2-3}N(C_{1-4}alkyl)$- or —$(CH_2)_{1-2}N(C_{1-4}alkyl)(CH_2)$—;
$R^r$ is selected from the group consisting of —OH, —$C_{1-6}$alkyl, —$OC_{1-6}$alkyl, phenyl, —Ophenyl, benzyl, —Obenzyl, —$C_{3-6}$cycloalkyl, —$OC_{3-6}$cycloalkyl, —CN, —$NO_2$, —$N(R^a)R^b$ (wherein $R^a$ and $R^b$ are independently selected from —H, —$C_{1-6}$alkyl or —$C_{1-6}$alkenyl, or $R^a$ and $R^b$ may be taken together with the nitrogen of attachment to form an otherwise aliphatic hydrocarbon ring, said ring having 4 to 7 members, optionally having one carbon replaced with >O, =N—, >NH or >N($C_{1-4}$ alkyl), optionally having one carbon substituted with —OH, and optionally having one or two double bonds in the ring), —(C=O)N($R^a$)$R^b$, —(N—$R^c$)COR$^c$, —(N—$R^c$)$SO_2C_{1-6}$alkyl (wherein $R^c$ is H or $C_{1-6}$alkyl or two $R^c$ in the same substituent may be taken together with the amide of attachment to form an otherwise aliphatic hydrocarbon ring, said ring having 4 to 6 members), —(C=O)$C_{1-6}$alkyl, —(S=(O)$_q$)—$C_{1-6}$ alkyl (wherein q is selected from 0, 1 or 2), —$SO_2N(R^a)R^b$, —$SCF_3$, halo, —$CF_3$, —$OCF_3$, and —$COOC_{1-6}$alkyl;
B) phenyl or pyridyl fused at two adjacent ring members to a three membered hydrocarbon moiety to form a fused five membered aromatic ring, which moiety has one carbon atom replaced by >O, >S, >NH or >N(C$_{1-4}$alkyl) and which moiety has up to one additional carbon atom optionally replaced by N, the fused rings optionally mono-, di- or tri-substituted with R$^r$;

C) phenyl fused at two adjacent ring members to a four membered hydrocarbon moiety to form a fused six membered aromatic ring, which moiety has one or two carbon atoms replaced by N, the fused rings optionally mono-, di- or tri-substituted with R$^r$;

D) naphthyl, optionally mono-, di- or tri-substituted with R$^r$;

E) a monocyclic aromatic hydrocarbon group having five ring atoms, having a carbon atom which is the point of attachment, having one carbon atom replaced by >O, >S, >NH or >N(C$_{1-4}$alkyl), having up to one additional carbon atoms optionally replaced by N, optionally mono- or di-substituted with R$^r$ and optionally benzo fused on the condition that two or fewer of said carbon ring atoms are replaced by a heteroatom, where the benzo fused moiety is optionally mono-, di- or tri-substituted with R$^r$; and F) a monocyclic aromatic hydrocarbon group having six ring atoms, having a carbon atom which is the point of attachment, having one or two carbon atoms replaced by N, optionally mono- or di-substituted with R$^r$ and optionally benzo fused, where the benzo fused moiety is optionally mono- or di-substituted with R$^r$;

R$^4$ is selected from the group consisting of;

I) —COOR$^5$, where R$^5$ is selected from the group consisting of —H and —C$_{1-4}$alkyl, and II) —CONR$^6$R$^7$, where R$^6$ and R$^7$ are independently selected from the group consisting of —H, —C$_{1-6}$alkyl and —C$_{3-6}$cycloalkyl optionally hydroxy substituted, or R$^6$ and R$^7$ may be taken together with the nitrogen of attachment to form an otherwise aliphatic hydrocarbon ring, said ring having 5 to 7 members, optionally having one carbon replaced with >O, =N—, >NH or >N(C$_{1-4}$alkyl) and optionally having one or two double bonds in the ring;

and enantiomers, diastereomers, hydrates, solvates and pharmaceutically acceptable salts, esters and amides thereof.

29. A method for the treatment of pain, drug dependence, anxiety, panic attack, schizophrenia, secretory disorder, gastrointestinal motility disorders, functional bowel disease, biliary colic, or anorexia in mammals comprising the step of administering to a mammal suffering there from a therapeutically effective amount of compound having CCK1 antagonist or inverse agonist activity of formula (I):

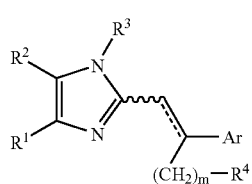

(I)

wherein,

R$^1$ and R$^2$ can be the same or different and are selected from the group consisting of;

a) phenyl, optionally mono-, di- or tri-substituted with R$^p$ or di-substituted on adjacent carbons with —OC$_{1-4}$alkyleneO—, —(CH$_2$)$_{2-3}$NH—, —(CH$_2$)$_{1-2}$NH(CH$_2$)—, —(CH$_2$)$_{2-3}$N(C$_{1-4}$alkyl)- or —(CH$_2$)$_{1-2}$N(C$_{1-4}$alkyl)(CH$_2$)—;

R$^p$ is selected from the group consisting of —OH, —C$_{1-6}$alkyl, —OC$_{1-6}$alkyl, phenyl, —Ophenyl, benzyl, —Obenzyl, —C$_{3-6}$cycloalkyl, —OC$_{3-6}$cycloalkyl, —CN, —NO$_2$, —N(R$^y$)R$^z$ (wherein R$^y$ and R$^z$ are independently selected from —H, —C$_{1-6}$alkyl or —C$_{1-6}$alkenyl, or R$^y$ and R$^z$ may be taken together with the nitrogen of attachment to form an otherwise aliphatic hydrocarbon ring, said ring having 4 to 7 members, optionally having one carbon replaced with >O, =N—, >NH or >N(C$_{1-4}$alkyl), optionally having one carbon substituted with —OH, and optionally having one or two double bonds in the ring), —(C=O)N(R$^y$)R$^z$, —(N—R$^t$)COR$^t$, —(N—R$^t$)SO$_2$C$_{1-6}$alkyl (wherein R$^t$ is —H or —C$_{1-6}$alkyl or two R$^t$ in the same substituent may be taken together with the amide of attachment to form an otherwise aliphatic hydrocarbon ring, said ring having 4 to 6 members), —(C=O)C$_{1-6}$alkyl, —(S=(O)$_n$)—C$_{1-6}$ alkyl (wherein n is selected from 0, 1 or 2), —SO$_2$N(R$^y$)R$^z$, —SCF$_3$, halo, —CF$_3$, —OCF$_3$, —COOH and —COOC$_{1-6}$alkyl;

b) phenyl or pyridyl fused at two adjacent ring members to a three membered hydrocarbon moiety to form a fused five membered aromatic ring, which moiety has one carbon atom replaced by >O, >S, >NH or >N(C$_{1-4}$alkyl) and which moiety has up to one additional carbon atom optionally replaced by N, the fused rings optionally mono-, di- or tri-substituted with R$^p$;

c) phenyl fused at two adjacent ring members to a four membered hydrocarbon moiety to form a fused six membered aromatic ring, which moiety has one or two carbon atoms replaced by N, the fused rings optionally mono-, di- or tri-substituted with R$^p$;

d) naphthyl, optionally mono-, di- or tri-substituted with R$^p$;

e) a monocyclic aromatic hydrocarbon group having five ring atoms, having a carbon atom which is the point of attachment, having one carbon atom replaced by >O, >S, >NH or >N(C$_{1-4}$alkyl), having up to one additional carbon atoms optionally replaced by N, optionally mono- or di-substituted with R$^p$ and optionally benzo fused, where the benzo fused moiety is optionally mono-, di- or tri-substituted with R$^p$; and f) a monocyclic aromatic hydrocarbon group having six ring atoms, having a carbon atom which is the point of attachment, having one or two carbon atoms replaced by N, having one N optionally oxidized to the N-oxide, optionally mono- or di-substituted with R$^p$ and optionally benzo fused, where the benzo fused moiety is optionally mono- or di-substituted with R$^p$;

R$^3$ is selected from the group consisting of —H and —C$_{1-6}$alkyl;

m is selected from 0, 1, or 2;

Ar is selected from the group consisting of:

A) phenyl, optionally mono-, di- or tri-substituted with R$^r$ or di-substituted on adjacent carbons with —OC$_{1-4}$ alkyleneO—, —(CH$_2$)$_{2-3}$NH—, —(CH$_2$)$_{1-2}$NH(CH$_2$)—, —(CH$_2$)$_{2-3}$N(C$_{1-4}$alkyl)- or —(CH$_2$)$_{1-2}$N(C$_{1-4}$alkyl)(CH$_2$)—;

R$^r$ is selected from the group consisting of —OH, —C$_{1-6}$alkyl, —OC$_{1-6}$alkyl, phenyl, —Ophenyl, benzyl, —Obenzyl, —C$_{3-6}$cycloalkyl, —OC$_{3-6}$cycloalkyl, —CN, —NO$_2$, —N(R$^a$)R$^b$ (wherein R$^a$ and R$^b$ are independently selected from —H, —C$_{1-6}$alkyl or —C$_{1-6}$alkenyl, or R$^a$ and R$^b$ may be taken together with the nitrogen of attachment to form an otherwise aliphatic hydrocarbon ring, said ring having 4 to 7 members, optionally having one carbon replaced with >O, =N—, >NH or >N(C$_{1-4}$alkyl), optionally having one carbon substituted with —OH, and optionally having one or two double bonds in the ring), —(C=O)N(R$^a$)R$^b$, —(N—R$^c$)COR$^c$, —(N—R$^c$)SO$_2$C$_{1-6}$alkyl (wherein R$^c$ is H or C$_{1-6}$alkyl or two R$^c$ in the same substituent may be taken together with the amide of attachment to form an otherwise aliphatic hydrocarbon ring, said ring having 4 to 6 members), —(C=O)C$_{1-6}$alkyl, —(S=(O)$_q$)—C$_{1-6}$alkyl (wherein q is selected from 0, 1 or 2), —SO$_2$N(R$^a$)R$^b$, —SCF$_3$, halo, —CF$_3$, —OCF$_3$, and —COOC$_{1-6}$alkyl;

B) phenyl or pyridyl fused at two adjacent ring members to a three membered hydrocarbon moiety to form a fused five membered aromatic ring, which moiety has one carbon atom replaced by >O, >S, >NH or >N(C$_{1-4}$alkyl) and which moiety has up to one additional carbon atom optionally replaced by N, the fused rings optionally mono-, di- or tri-substituted with R$^r$;

C) phenyl fused at two adjacent ring members to a four membered hydrocarbon moiety to form a fused six membered aromatic ring, which moiety has one or two carbon atoms replaced by N, the fused rings optionally mono-, di- or tri-substituted with R$^r$;

D) naphthyl, optionally mono-, di- or tri-substituted with R$^r$;

E) a monocyclic aromatic hydrocarbon group having five ring atoms, having a carbon atom which is the point of attachment, having one carbon atom replaced by >O, >S, >NH or >N(C$_{1-4}$alkyl), having up to one additional carbon atoms optionally replaced by N, optionally mono- or di-substituted with R$^r$ and optionally benzo fused on the condition that two or fewer of said carbon ring atoms are replaced by a heteroatom, where the benzo fused moiety is optionally mono-, di- or tri-substituted with R$^r$; and F) a monocyclic aromatic hydrocarbon group having six ring atoms, having a carbon atom which is the point of attachment, having one or two carbon atoms replaced by N, optionally mono- or di-substituted with R$^r$ and optionally benzo fused, where the benzo fused moiety is optionally mono- or di-substituted with R$^r$;

R$^4$ is selected from the group consisting of;

I) —COOR$^5$, where R$^5$ is selected from the group consisting of —H and —C$_{1-4}$alkyl, and II) —CONR$^6$R$^7$, where R$^6$ and R$^7$ are independently selected from the group consisting of —H, —C$_{1-6}$alkyl and —C$_{3-6}$cycloalkyl optionally hydroxy substituted, or R$^6$ and R$^7$ may be taken together with the nitrogen of attachment to form an otherwise aliphatic hydrocarbon ring, said ring having 5 to 7 members, optionally having one carbon replaced with >O, =N—, >NH or >N(C$_{1-4}$alkyl) and optionally having one or two double bonds in the ring;

and enantiomers, diastereomers, hydrates, solvates and pharmaceutically acceptable salts, esters and amides thereof.

30. A method for the treatment or prevention of obesity, hypervigilance or gallstones in mammals comprising the step of administering to a mammal suffering there from a therapeutically effective amount of compound having CCK1 agonist activity of formula (I):

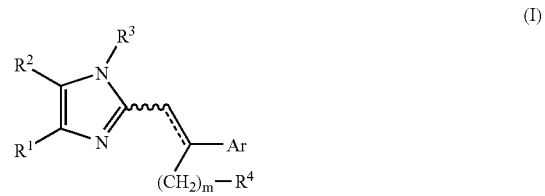

(I)

wherein,

R$^1$ and R$^2$ can be the same or different and are selected from the group consisting of;

a) phenyl, optionally mono-, di- or tri-substituted with R$^p$ or di-substituted on adjacent carbons with —OC$_{1-4}$alkyleneO—, —(CH$_2$)$_{2-3}$NH—, —(CH$_2$)$_{1-2}$NH(CH$_2$)—, —(CH$_2$)$_{2-3}$N(C$_{1-4}$alkyl)- or —(CH$_2$)$_{1-2}$N(C$_{1-4}$alkyl)(CH$_2$)—;

R$^p$ is selected from the group consisting of —OH, —C$_{1-6}$alkyl, —OC$_{1-6}$alkyl, phenyl, —Ophenyl, benzyl, —Obenzyl, —C$_{3-6}$cycloalkyl, —OC$_{3-6}$cycloalkyl, —CN, —NO$_2$, —N(R$^y$)R$^z$ (wherein R$^y$ and R$^z$ are independently selected from —H, —C$_{1-6}$alkyl or —C$_{1-6}$alkenyl, or R$^y$ and R$^z$ may be taken together with the nitrogen of attachment to form an otherwise aliphatic hydrocarbon ring, said ring having 4 to 7 members, optionally having one carbon replaced with >O, =N—, >NH or >N(C$_{1-4}$alkyl), optionally having one carbon substituted with —OH, and optionally having one or two double bonds in the ring), —(C=O)N(R$^y$)R$^z$, —(N—R$^t$)COR$^t$, —(N—R$^t$)SO$_2$C$_{1-6}$alkyl (wherein R$^t$ is —H or —C$_{1-6}$alkyl or two R$^t$ in the same substituent may be taken together with the amide of attachment to form an otherwise aliphatic hydrocarbon ring, said ring having 4 to 6 members), —(C=O)C$_{1-6}$alkyl, —(S=(O)$_n$)—C$_{1-6}$alkyl (wherein n is selected from 0, 1 or 2), —SO$_2$N(R$^y$)R$^z$, —SCF$_3$, halo, —CF$_3$, —OCF$_3$, —COOH and —COOC$_{1-6}$alkyl;

b) phenyl or pyridyl fused at two adjacent ring members to a three membered hydrocarbon moiety to form a fused five membered aromatic ring, which moiety has one carbon atom replaced by >O, >S, >NH or >N(C$_{1-4}$alkyl) and which moiety has up to one additional carbon atom optionally replaced by N, the fused rings optionally mono-, di- or tri-substituted with R$^p$;

c) phenyl fused at two adjacent ring members to a four membered hydrocarbon moiety to form a fused six membered aromatic ring, which moiety has one or two carbon atoms replaced by N, the fused rings optionally mono-, di- or tri-substituted with R$^p$;

d) naphthyl, optionally mono-, di- or tri-substituted with R$^p$;

e) a monocyclic aromatic hydrocarbon group having five ring atoms, having a carbon atom which is the point of attachment, having one carbon atom replaced by >O, >S, >NH or >N(C$_{1-4}$alkyl), having up to one additional carbon atoms optionally replaced by N, optionally mono- or di-substituted with $R^p$ and optionally benzo fused, where the benzo fused moiety is optionally mono-, di- or tri-substituted with $R^p$; and f) a monocyclic aromatic hydrocarbon group having six ring atoms, having a carbon atom which is the point of attachment, having one or two carbon atoms replaced by N, having one N optionally oxidized to the N-oxide, optionally mono- or di-substituted with $R^p$ and optionally benzo fused, where the benzo fused moiety is optionally mono- or di-substituted with $R^p$;

$R^3$ is selected from the group consisting of —H and —$C_{1-6}$alkyl;

m is selected from 0, 1, or 2;

Ar is selected from the group consisting of:

A) phenyl, optionally mono-, di- or tri-substituted with $R^r$ or di-substituted on adjacent carbons with —$OC_{1-4}$ alkyleneO—, —$(CH_2)_{2-3}NH$—, —$(CH_2)_{1-2}NH(CH_2)$—, —$(CH_2)_{2-3}N(C_{1-4}alkyl)$- or —$(CH_2)_{1-2}N(C_{1-4}alkyl)(CH_2)$—;

$R^r$ is selected from the group consisting of —OH, —$C_{1-6}$alkyl, —$OC_{1-6}$alkyl, phenyl, —Ophenyl, benzyl, —Obenzyl, —$C_{3-6}$cycloalkyl, —$OC_{3-6}$cycloalkyl, —CN, —$NO_2$, —$N(R^a)R^b$ (wherein $R^a$ and $R^b$ are independently selected from —H, —$C_{1-6}$alkyl or —$C_{1-6}$alkenyl, or $R^a$ and $R^b$ may be taken together with the nitrogen of attachment to form an otherwise aliphatic hydrocarbon ring, said ring having 4 to 7 members, optionally having one carbon replaced with >O, =N—, >NH or >$N(C_{1-4}$alkyl), optionally having one carbon substituted with —OH, and optionally having one or two double bonds in the ring), —(C=O)$N(R^a)R^b$, —(N—$R^c$)$COR^c$, —(N—$R^c$)$SO_2C_{1-6}$alkyl (wherein $R^c$ is H or $C_{1-6}$alkyl or two $R^c$ in the same substituent may be taken together with the amide of attachment to form an otherwise aliphatic hydrocarbon ring, said ring having 4 to 6 members), —(C=O)$C_{1-6}$alkyl, —(S=(O)$_q$)—$C_{1-6}$alkyl (wherein q is selected from 0, 1 or 2), —$SO_2N(R^a)R^b$, —$SCF_3$, halo, —$CF_3$, —$OCF_3$, and —$COOC_{1-6}$alkyl;

B) phenyl or pyridyl fused at two adjacent ring members to a three membered hydrocarbon moiety to form a fused five membered aromatic ring, which moiety has one carbon atom replaced by >O, >S, >NH or >$N(C_{1-4}$alkyl) and which moiety has up to one additional carbon atom optionally replaced by N, the fused rings optionally mono-, di- or tri-substituted with $R^r$;

C) phenyl fused at two adjacent ring members to a four membered hydrocarbon moiety to form a fused six membered aromatic ring, which moiety has one or two carbon atoms replaced by N, the fused rings optionally mono-, di- or tri-substituted with $R^r$;

D) naphthyl, optionally mono-, di- or tri-substituted with $R^r$;

E) a monocyclic aromatic hydrocarbon group having five ring atoms, having a carbon atom which is the point of attachment, having one carbon atom replaced by >O, >S, >NH or >$N(C_{1-4}$alkyl), having up to one additional carbon atoms optionally replaced by N, optionally mono- or di-substituted with $R^r$ and optionally benzo fused on the condition that two or fewer of said carbon ring atoms are replaced by a heteroatom, where the benzo fused moiety is optionally mono-, di- or tri-substituted with $R^r$; and F) a monocyclic aromatic hydrocarbon group having six ring atoms, having a carbon atom which is the point of attachment, having one or two carbon atoms replaced by N, optionally mono- or di-substituted with $R^r$ and optionally benzo fused, where the benzo fused moiety is optionally mono- or di-substituted with $R^r$;

$R^4$ is selected from the group consisting of;

I) —$COOR^5$, where $R^5$ is selected from the group consisting of —H and —$C_{1-4}$alkyl, and II) —$CONR^6R^7$, where $R^6$ and $R^7$ are independently selected from the group consisting of —H, —$C_{1-6}$alkyl and —$C_{3-6}$cycloalkyl optionally hydroxy substituted, or $R^6$ and $R^7$ may be taken together with the nitrogen of attachment to form an otherwise aliphatic hydrocarbon ring, said ring having 5 to 7 members, optionally having one carbon replaced with >O, =N—, >NH or >$N(C_{1-4}$alkyl) and optionally having one or two double bonds in the ring;

and enantiomers, diastereomers, hydrates, solvates and pharmaceutically acceptable salts, esters and amides thereof.

* * * * *